(12) United States Patent
Yeung et al.

(10) Patent No.: US 8,562,673 B2
(45) Date of Patent: Oct. 22, 2013

(54) STENTED TRANSCATHETER PROSTHETIC HEART VALVE DELIVERY SYSTEM AND METHOD

(75) Inventors: Hubert Yeung, Santa Rosa, CA (US); John Shanahan, Santa Rosa, CA (US); Joshua Dwork, Santa Rosa, CA (US); Adam Shipley, San Rafael, CA (US); Jeffrey Allen, Santa Rosa, CA (US); Susheel Deshmukh, Santa Rosa, CA (US); Kishore Udipi, Santa Rosa, CA (US); Ya Guo, Santa Rosa, CA (US)

(73) Assignee: Medtronic, Inc., Minneapolis, MN (US)

( * ) Notice: Subject to any disclaimer, the term of this patent is extended or adjusted under 35 U.S.C. 154(b) by 307 days.

(21) Appl. No.: 12/886,975

(22) Filed: Sep. 21, 2010

(65) Prior Publication Data

US 2011/0098804 A1  Apr. 28, 2011

Related U.S. Application Data

(60) Provisional application No. 61/244,344, filed on Sep. 21, 2009.

(51) Int. Cl.
  *A61F 2/24*  (2006.01)
(52) U.S. Cl.
  USPC ........................................ 623/2.11; 623/1.12
(58) Field of Classification Search
  USPC .......... 623/1.11, 1.12, 1.23, 2.11, 2.17, 2.18, 623/904; 606/151, 153–156, 191, 198, 200, 606/108
  See application file for complete search history.

(56) References Cited

U.S. PATENT DOCUMENTS

| | | | |
|---|---|---|---|
| 5,683,431 A | 11/1997 | Wang | |
| 5,824,041 A | 10/1998 | Lenker et al. | |
| 5,906,619 A | 5/1999 | Olson et al. | |
| 5,957,949 A | 9/1999 | Leonhardt et al. | |
| 7,018,406 B2 * | 3/2006 | Seguin et al. | 623/2.1 |
| 2003/0199963 A1 | 10/2003 | Tower et al. | |
| 2005/0137688 A1 | 6/2005 | Salahieh et al. | |
| 2006/0004439 A1 | 1/2006 | Spenser et al. | |
| 2006/0052867 A1 | 3/2006 | Revuelta et al. | |
| 2006/0121080 A1 * | 6/2006 | Lye et al. | 424/423 |
| 2006/0259136 A1 | 11/2006 | Nguyen et al. | |
| 2006/0265056 A1 | 11/2006 | Nguyen et al. | |

(Continued)

FOREIGN PATENT DOCUMENTS

| | | |
|---|---|---|
| EP | 0 812 579 | 12/1997 |
| EP | 1 656 963 | 5/2006 |

(Continued)

*Primary Examiner* — Corrine M McDermott
*Assistant Examiner* — Robert Lynch

(57) ABSTRACT

A percutaneous stented valve delivery device including an inner shaft, a sheath, and a delivery capsule. The sheath slidably receives the inner shaft. A capsule proximal zone is attached to the sheath. A capsule distal zone is configured to transition between normal and flared states. A diameter of the distal zone is greater in the flared state, and the capsule includes a shape memory component that naturally assumes the normal state. The device is operable to perform a reversible partial deployment procedure in which a portion of the prosthesis is exposed distal the capsule and allowed to radially expand. Subsequently, with distal advancement of the capsule, the distal zone transitions to the flared state and imparts a collapsing force onto the prosthesis, causing the prosthesis to radially collapse and become recaptured within the delivery capsule. The capsule can include a laser cut tube encapsulated by a polymer.

14 Claims, 23 Drawing Sheets

(56) References Cited

U.S. PATENT DOCUMENTS

| | | |
|---|---|---|
| 2007/0005131 A1 | 1/2007 | Taylor |
| 2007/0088431 A1 | 4/2007 | Bourang et al. |
| 2007/0239266 A1 | 10/2007 | Birdsall |
| 2007/0239269 A1 | 10/2007 | Dolan et al. |
| 2008/0065011 A1 | 3/2008 | Marchand et al. |
| 2008/0082165 A1 | 4/2008 | Wilson et al. |
| 2008/0147160 A1 | 6/2008 | Ghione et al. |
| 2008/0147181 A1 | 6/2008 | Ghione et al. |
| 2008/0154351 A1* | 6/2008 | Leewood et al. ............... 623/1.2 |
| 2008/0188928 A1 | 8/2008 | Salahieh et al. |
| 2009/0093876 A1 | 4/2009 | Nitzan et al. |
| 2009/0138079 A1 | 5/2009 | Tuval et al. |
| 2009/0171447 A1 | 7/2009 | Von Segesser et al. |
| 2009/0177275 A1 | 7/2009 | Case |
| 2009/0281619 A1 | 11/2009 | Le et al. |
| 2010/0094411 A1 | 4/2010 | Tuval et al. |
| 2010/0121434 A1 | 5/2010 | Paul et al. |

FOREIGN PATENT DOCUMENTS

| | | |
|---|---|---|
| GB | 2433700 | 4/2007 |
| WO | 03/005936 | 1/2003 |
| WO | 2008/138584 | 11/2008 |
| WO | 2009/091509 | 7/2009 |

* cited by examiner

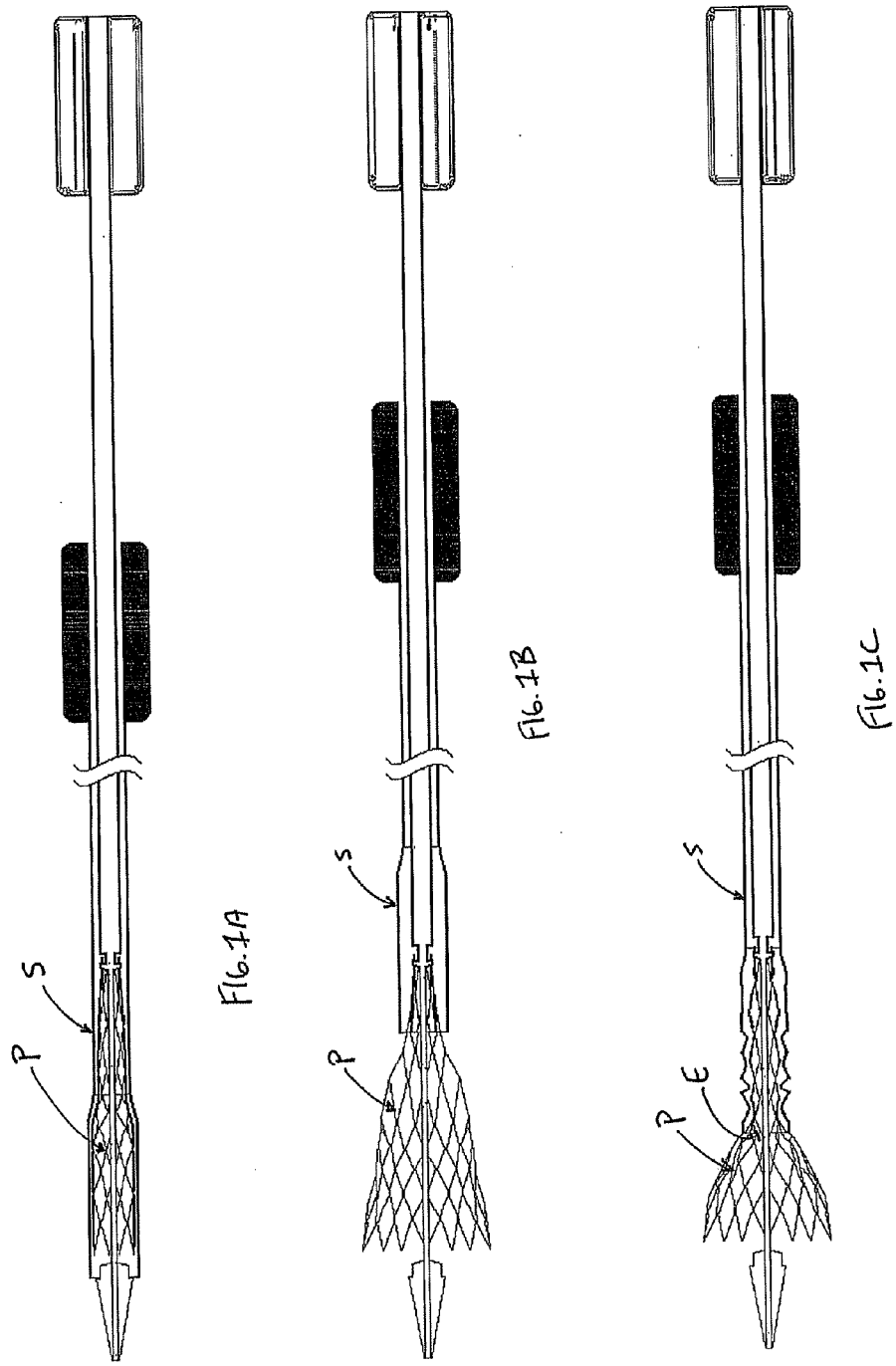

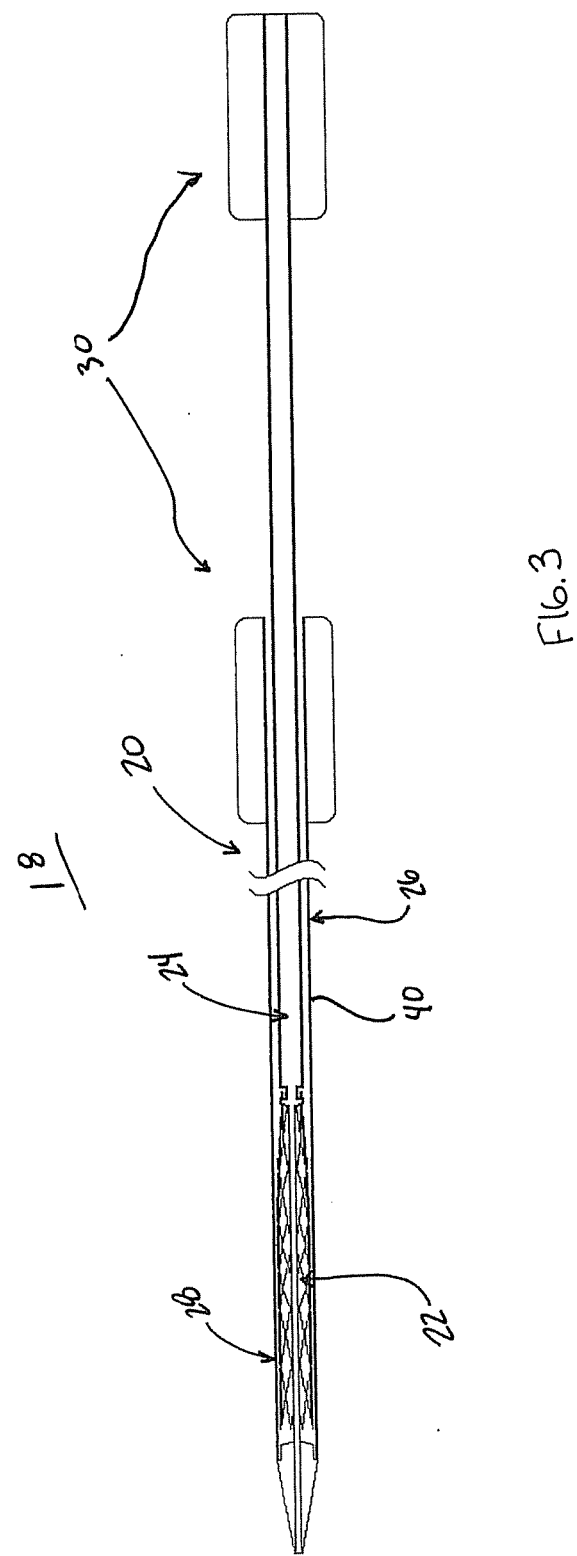

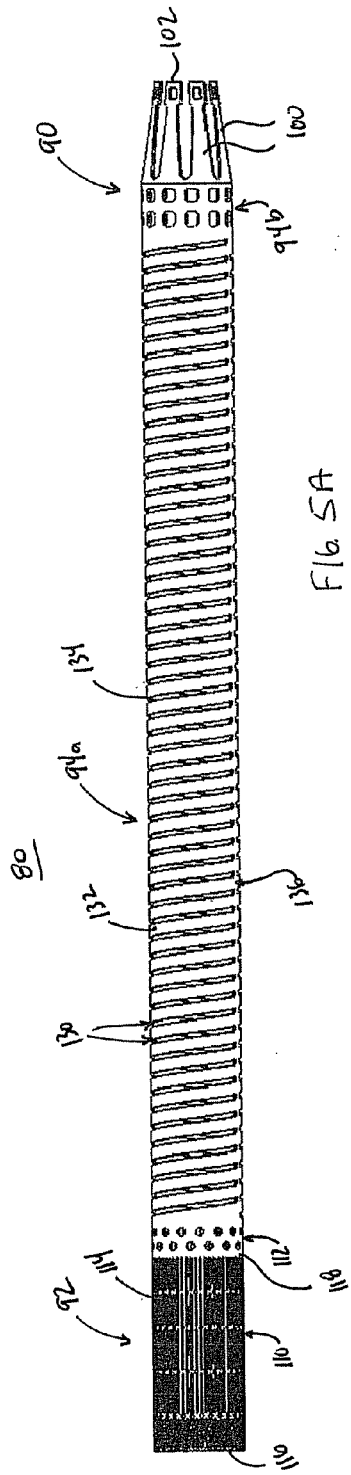
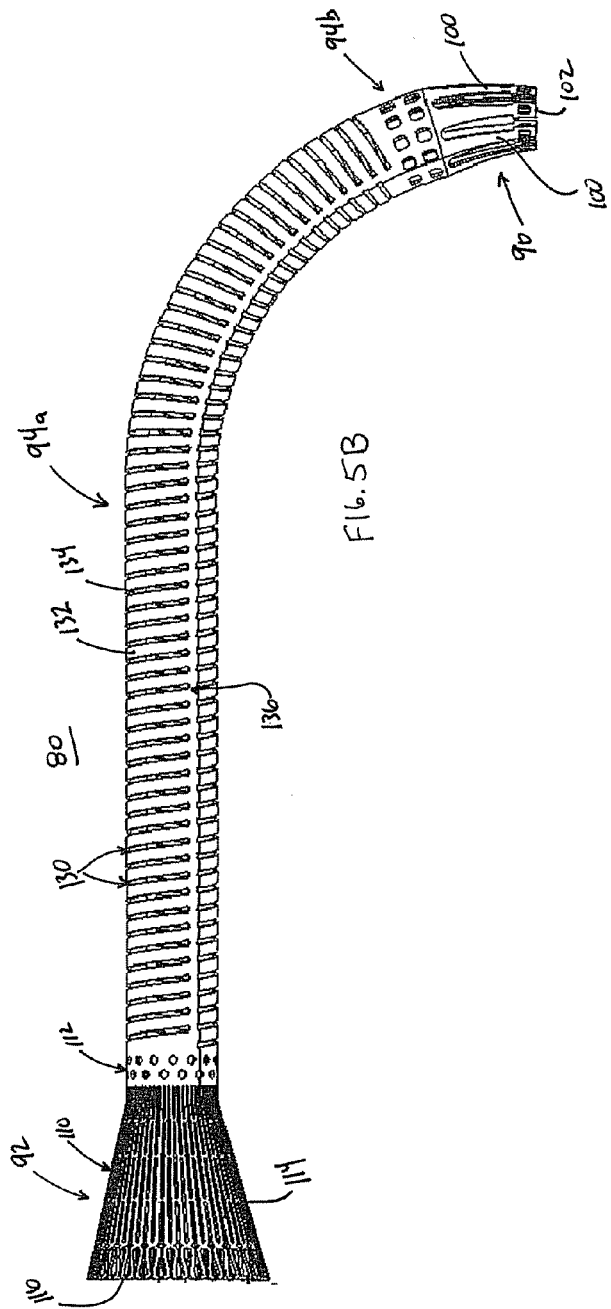

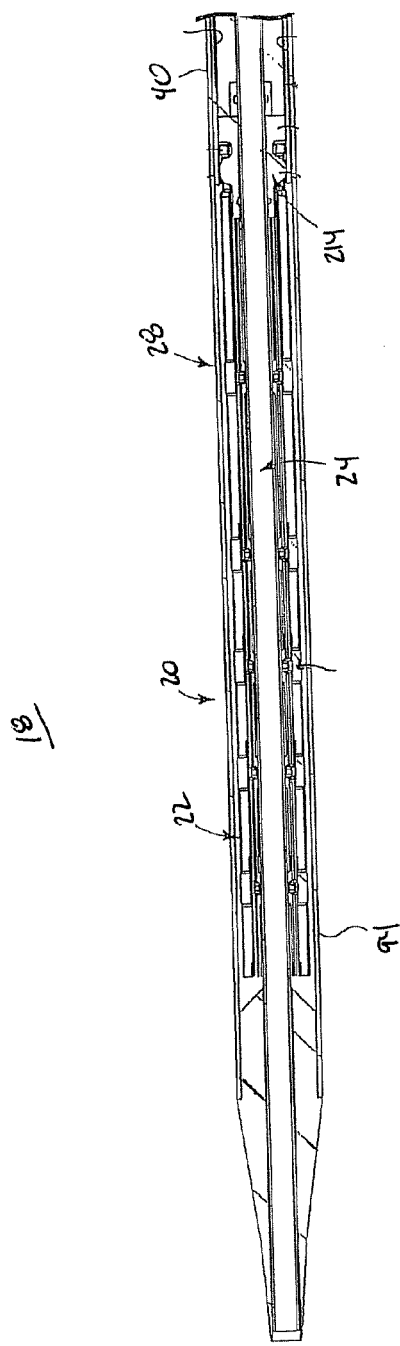
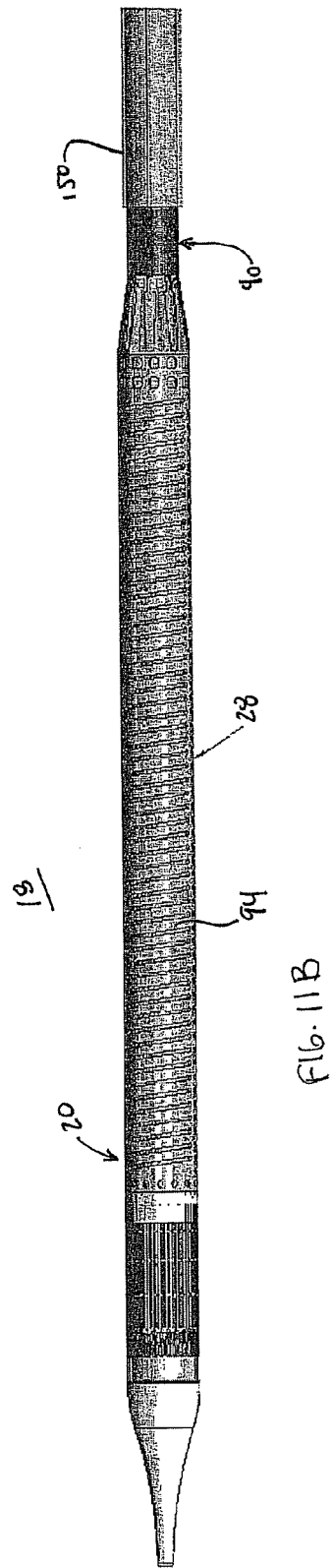
FIG. 11A
FIG. 11B

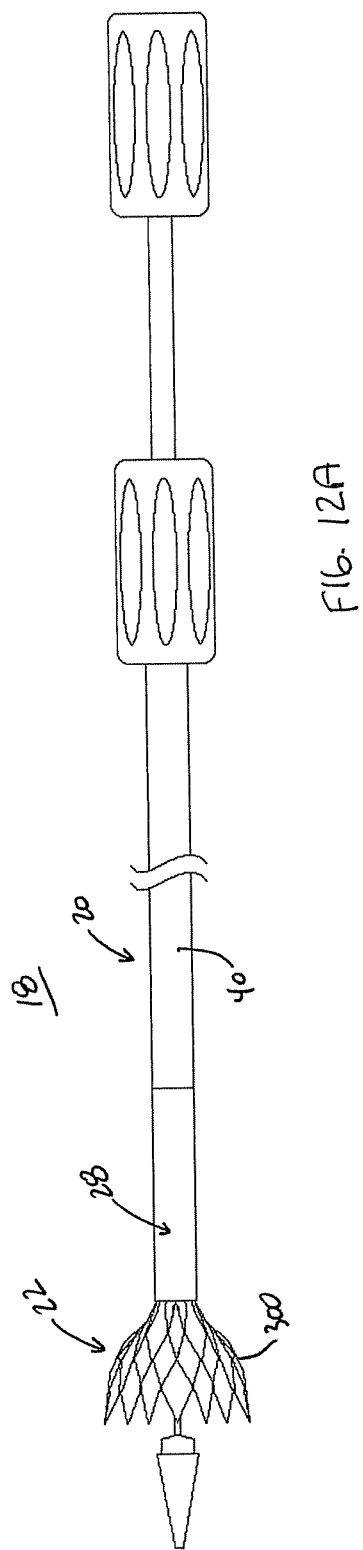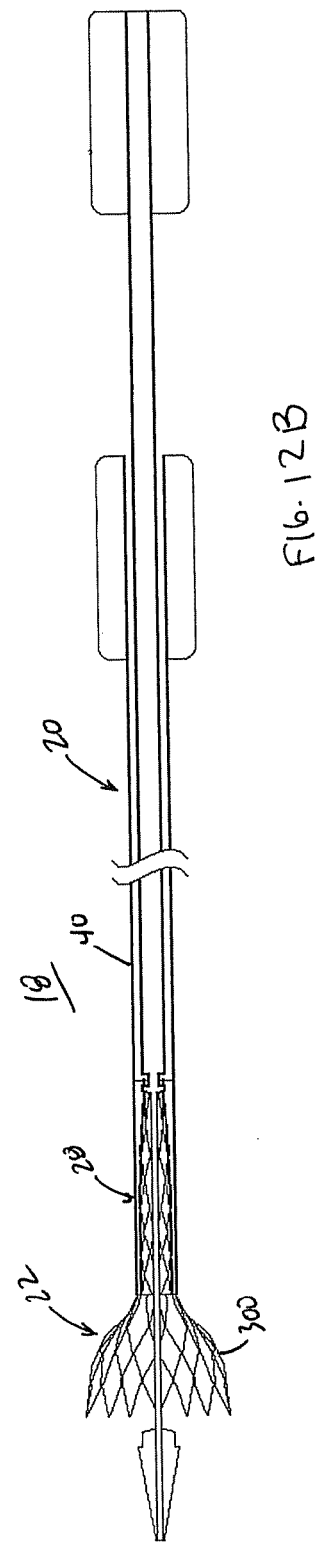

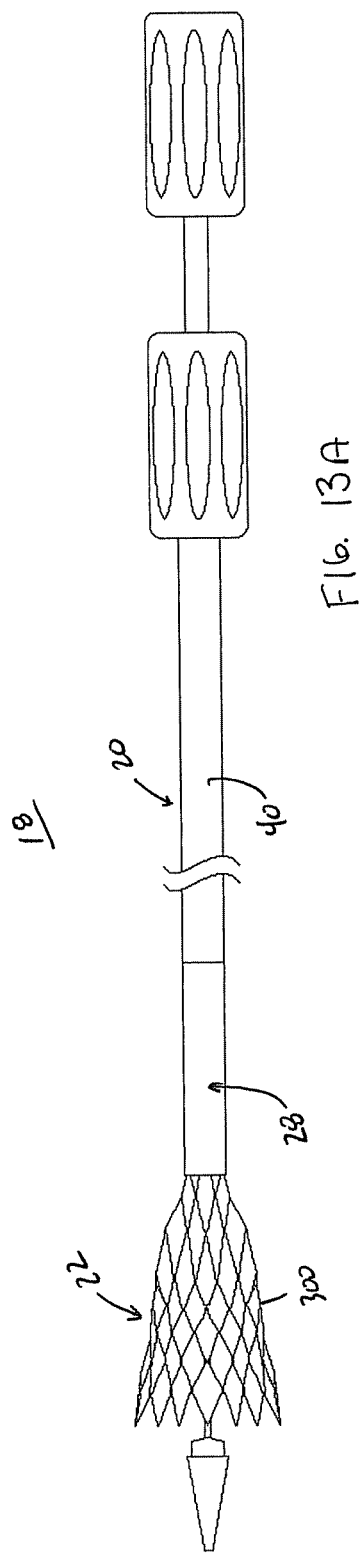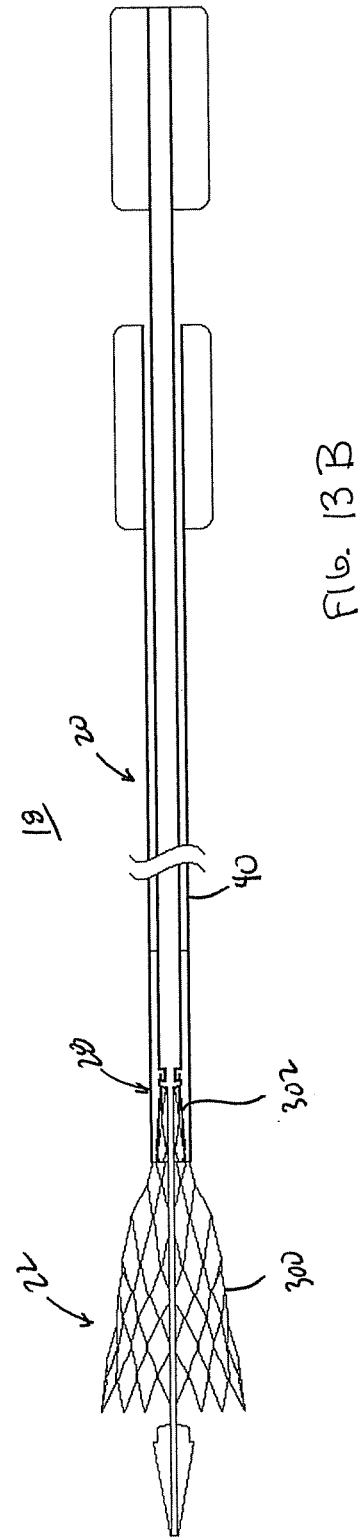

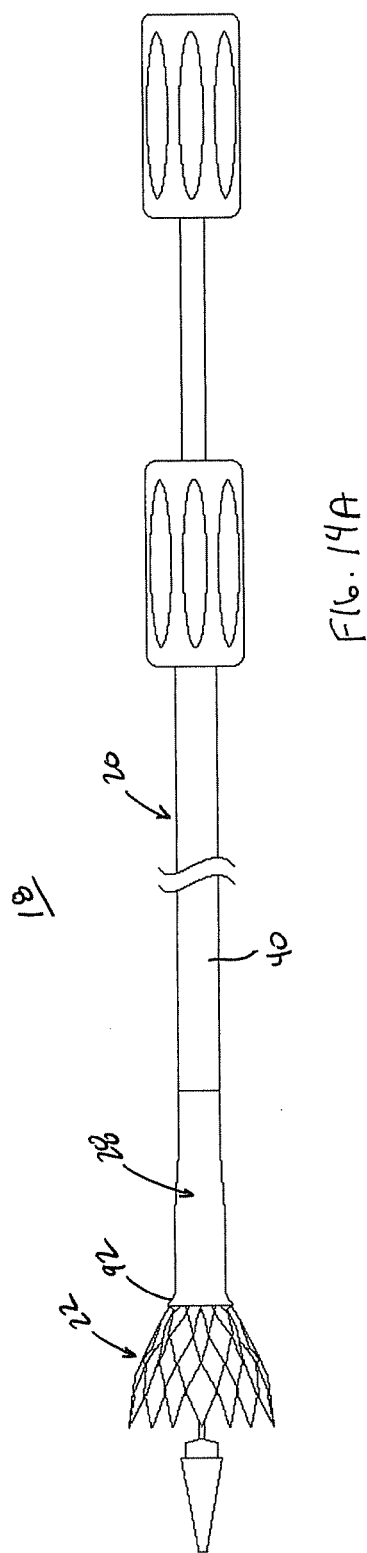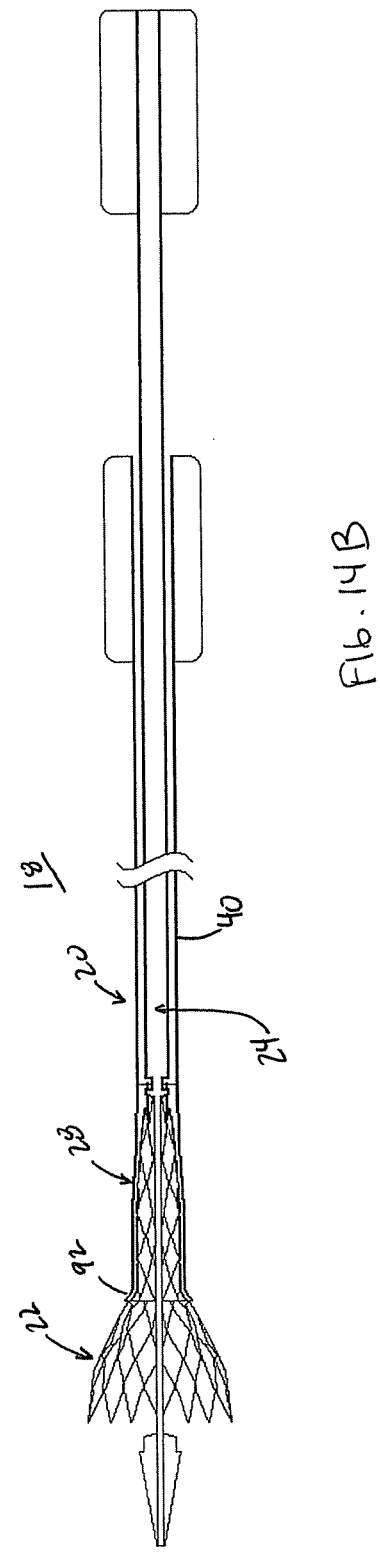

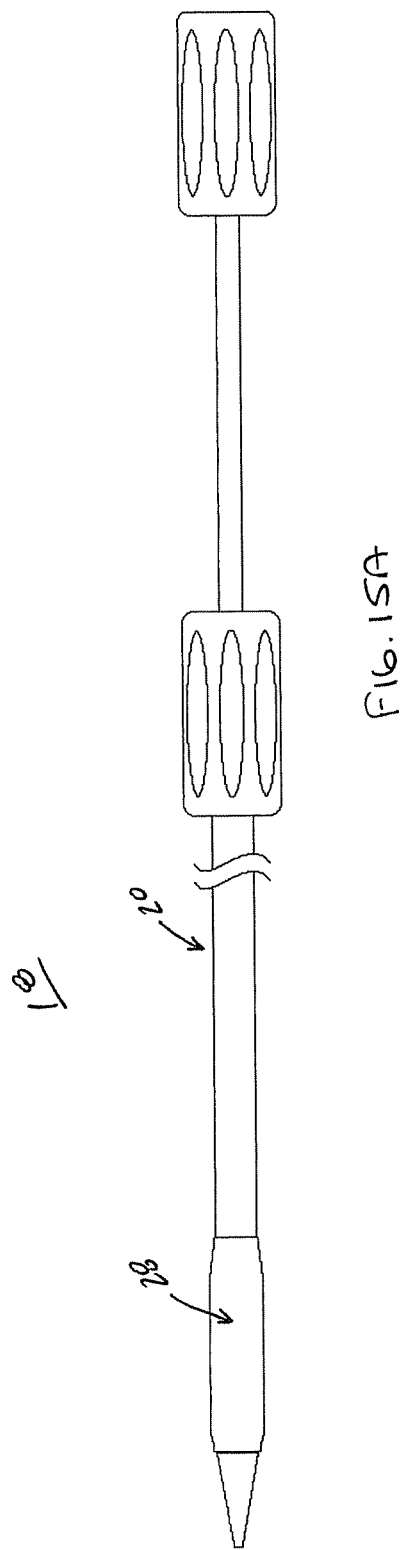
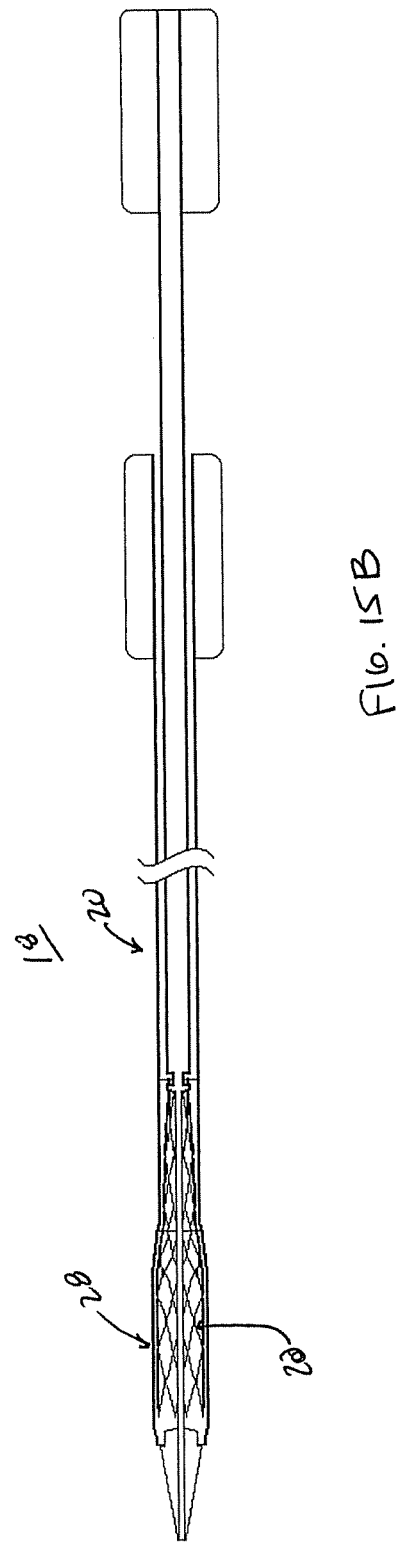
FIG. 15A
FIG. 15B

STENTED TRANSCATHETER PROSTHETIC HEART VALVE DELIVERY SYSTEM AND METHOD

CROSS-REFERENCE TO RELATED APPLICATIONS

This application claims priority under 35 U.S.C. §119(e)(1) to U.S. Provisional Patent Application Ser. No. 61/244,344, filed Sep. 21, 2009, entitled "Stented Transcatheter Prosthetic Heart Valve Delivery System and Method", the entire teachings of which are incorporated herein by reference.

BACKGROUND

The present disclosure relates to systems, devices, and methods for percutaneous implantation of a heart valve prosthesis. More particularly, it relates to systems, devices, and methods for transcatheter implantation of a stented prosthetic heart valve, including partial deployment, recapturing and repositioning of the prosthesis at the implantation site.

Diseased or otherwise deficient heart valves can be repaired or replaced with an implanted prosthetic heart valve. The terms "repair" and "replace" are used interchangeably throughout the specification, and a reference to "repair" of a defective native heart valve is inclusive of a prosthetic heart valve that renders the native leaflets non-functional, or that leaves the native leaflets intact and functional. Conventionally, heart valve replacement surgery is an open-heart procedure conducted under general anesthesia, during which the heart is stopped and blood flow is controlled by a heart-lung bypass machine. Traditional open surgery inflicts significant patient trauma and discomfort, and exposes the patient to a number of potential risks, such as infection, stroke, renal failure, and adverse effects associated with the use of the heart-lung bypass machine, for example.

Due to the drawbacks of open-heart surgical procedures, there has been an increased interest in minimally invasive and percutaneous replacement of cardiac valves. With percutaneous transcatheter (or transluminal) techniques, a valve prosthesis is compacted for delivery in a catheter and then advanced, for example, through an opening in the femoral artery and through the descending aorta to the heart, where the prosthesis is then deployed in the annulus of the valve to be restored (e.g., the aortic valve annulus). Although transcatheter techniques have attained widespread acceptance with respect to the delivery of conventional stents to restore vessel patency, only mixed results have been realized with percutaneous delivery of the more complex prosthetic heart valve.

Various types and configurations of prosthetic heart valves are available for percutaneous valve replacement procedures, and continue to be refined. The actual shape and configuration of any particular prosthetic heart valve is dependent to some extent upon the native shape and size of the valve being repaired (i.e., mitral valve, tricuspid valve, aortic valve, or pulmonary valve). In general, prosthetic heart valve designs attempt to replicate the functions of the valve being replaced and thus will include valve leaflet-like structures. With a bioprostheses construction, the replacement valve may include a valved vein segment that is mounted in some manner within an expandable stent frame to make a valved stent (or "stented prosthetic heart valve"). For many percutaneous delivery and implantation devices, the stent frame of the valved stent is made of a self-expanding material and construction. With these devices, the valved stent is crimped down to a desired size and held in that compressed arrangement within an outer sheath, for example. Retracting the sheath from the valved stent allows the stent to self-expand to a larger diameter, such as when the valved stent is in a desired position within a patient. In other percutaneous implantation devices, the valved stent can be initially provided in an expanded or uncrimped condition, then crimped or compressed on a balloon portion of catheter until it is as close to the diameter of the catheter as possible. Once delivered to the implantation site, the balloon in inflated to deploy the prosthesis. With either of these types of percutaneous stented prosthetic heart valve delivery devices, conventional sewing of the prosthetic heart valve to the patient's native tissue is typically not necessary.

It is imperative that the stented prosthetic heart valve be accurately located relative to the native annulus immediately prior to full deployment from the catheter as successful implantation requires the prosthetic heart valve intimately lodge and seal against the native annulus. If the prosthesis is incorrectly positioned relative to the native annulus, serious complications can result as the deployed device can leak and may even dislodge from the native valve implantation site. As a point of reference, this same concern does not arise in the context of other vascular stents; with these procedures, if the target site is "missed," another stent is simply deployed to "make-up" the difference.

While imaging technology can be employed as part of the implantation procedure to assist a clinician in better evaluating a location of the transcatheter prosthetic heart valve immediately prior to deployment, in many instances, this evaluation alone is insufficient. Instead, clinicians desire the ability to partially deploy the prosthesis, evaluate a position relative to the native annulus, and then reposition the prosthesis prior to full deployment if deemed necessary. Repositioning, in turn, requires the prosthesis first be re-compressed and re-located back within the outer delivery sheath. Stated otherwise, the partially deployed stented prosthetic heart valve must be "recaptured" by the delivery device, and in particular within the outer sheath. While, in theory, the recapturing of a partially deployed stented prosthetic heart valve is straight forward, in actual practice, the constraints presented by the implantation site and the stented heart valve itself render the technique exceedingly difficult.

For example, the stented heart valve is purposefully designed to rigidly resist collapsing forces once deployed to properly anchor itself in the anatomy of the heart. Thus, the delivery device component (e.g., outer delivery sheath) employed to force a partially-deployed segment of the prosthesis back to a collapsed arrangement must be capable of exerting a significant radial force. Conversely, however, the component cannot be overly rigid so as to avoid damaging the transcatheter heart valve as part of a recapturing procedure. Along these same lines, the aortic arch must be traversed, necessitating that the delivery device provide sufficient articulation attributes. Unfortunately, existing delivery devices do not consider, let alone optimally address, these and other issues.

As mentioned above, an outer sheath or catheter is conventionally employed to deliver a self-deploying vascular stent. Applying this same technique for the delivery of a self-deploying stented prosthetic heart valve, the high radial expansion force associated with the prosthesis is not problematic for complete deployment as the outer sheath is simply retracted in tension to allow the prosthetic heart valve to deploy. Were the conventional delivery device operated to only partially withdraw the outer sheath relative to the prosthesis, only the so-exposed distal region of the prosthetic would expand while the proximal region remained coupled to the delivery device. In theory, the outer sheath could simply be advanced distally to recapture the expanded region. Unfortunately, with conventional sheath configurations, attempting to compress the expanded region of the stented prosthetic heart valve by distally sliding the sheath is unlikely to be successful. The conventional delivery sheath cannot readily overcome the radial force of the expanded region of the prosthesis because, in effect, the sheath is placed into compression and will collapse due at least in part to the abrupt edge of the sheath being unable to cleanly slide over the expanded region of the prosthesis. This effect is illustrated in a simplified form in FIGS. 1A-1C. Prior to deployment (FIG. 1A), the stented prosthetic heart valve P is constrained within, and supports, the sheath S. With deployment (FIG. 1B), the sheath S is distally retracted, and the prosthesis P partially deploys. Were an attempt made to "recapture" the prosthesis P by distally sliding the sheath (FIG. 1C), a leading end E of the sheath S would abruptly abut against the enlarged diameter of the prosthesis P, such that the distal end E cannot readily slide over the prosthesis P. Further, the sheath S is no longer internally supported and the radially expanded bias of the prosthesis P will cause the sheath S to buckle or collapse.

Another concern presented by stented heart valve in situ recapturing is infolding. Infolding is defined as the prosthetic heart valve (and in particular the stent frame) folding into itself during the resheathing process. Basically, if the sheath or catheter component utilized to effectuate resheathing is overtly rigid (longitudinal) at the distal end, an excessive crimping force is applied; due to possible inherent cell instability of the stent frame, a section of the stent frame may fold non-uniformly, resulting in stent folding into itself. For example, FIGS. 2A-2D are simplified end views (e.g., inflow end) of a stented prosthetic heart valve P being resheathed or transitioned from a natural or expanded arrangement (FIG. 2A) to a contracted arrangement (FIG. 2D). As shown, during the stages of recapture, a cell section C of the valve stent frame P collapses non-uniformly, folding into itself. Infolding may damage the stent frame, decrease full deployment predictability, etc.

In light of the above, a need exists for a stented transcatheter prosthetic heart valve delivery system, device, and method that satisfies the constraints associated with heart valve implantation and permits partial deployment and recapturing of the prosthesis.

SUMMARY

Some aspects in accordance with principles of the present disclosure relate to a delivery device for percutaneously deploying a stented prosthetic heart valve. The device includes an inner shaft assembly, a sheath, and a tubular delivery capsule. The inner shaft assembly defines a distal tip, a proximal end, and an intermediate portion providing a coupling structure configured to selectively engage a stented prosthetic heart valve. The sheath forms a lumen sized to slidably receive at least the intermediate portion of the inner shaft, and terminates at a distal region. The tubular delivery capsule is formed separately from the sheath and define a proximal zone and a distal zone. The proximal zone is attached to the distal region of the sheath. The distal zone terminates at a distal end, and is configured to transition between a normal or relaxed state and a flared state. A diameter of the distal end is greater in the flared state than in the normal state. Further, the capsule includes a shape memory component constructed to naturally assume the normal state. With this construction, the device is configured to slidably receive a stented prosthetic heat valve within the delivery capsule and is operable to perform a reversible partial deployment procedure in which a portion of the stented prosthetic heart valve is exposed distal the capsule and allowed to radially expand. Subsequently, with distal advancement of the capsule relative to the prosthesis, the distal zone transitions to the flared state and imparts a collapsing force onto the prosthesis, causing the prosthesis to radially collapse. In some embodiments, the capsule includes a laser cut tube encapsulated by a polymer. In related embodiments, the laser cut tube forms an intermediate zone exhibiting elevated radial flexibility as compared to at least the distal zone, and optionally forms opposing longitudinal spines providing columnar strength.

Yet other aspects in accordance with principles of the present disclosure relate to a method of deploying a stented heart valve prosthesis to an implantation site. The method includes removably loading a stented heart valve prosthesis to a delivery device. The delivery device includes an inner shaft, a sheath, and a tubular delivery capsule. The delivery capsule has a proximal zone attached to and extending from a distal region of the sheath, as well as a distal zone opposite the proximal zone. Further, the prosthesis is coupled to the inner shaft and is slidably received within the delivery capsule such that the delivery device retains the prosthesis in a collapsed arrangement. The stented heart valve prosthesis is delivered, in the collapsed arrangement, through a bodily lumen and to the implantation site via the delivery device. The delivery capsule is proximally retracted relative to the prosthesis such that a distal portion of the prosthesis is exposed distal the capsule. In this regard, the distal portion self-expands toward a normal or expanded arrangement and at least a proximal portion of the stented prosthetic heart valve is retained within the delivery device in the collapsed state. A position of the prosthesis relative the implantation site is evaluated. Under circumstances where the evaluation indicates that the prosthesis is not correctly positioned, the sheath and the delivery capsule are distally advanced relative to the prosthesis. In this regard, the distal zone circumferentially flares about the stented heart valve prosthesis with the distal movement while simultaneously imparting a collapsing force onto a contacted region of the prosthesis, causing the contacted region to transition toward the collapsed arrangement. Finally, the delivery capsule is fully proximally retracted from the prosthesis such that the prosthesis deploys from the inner shaft. In some embodiments, flaring of the distal zone reduces retraction forces and instability, and provides sufficient axial strength so as to not buckle during the recapture step.

BRIEF DESCRIPTION OF THE DRAWINGS

FIGS. 1A-1C are simplified side views illustrating deficiencies of existing stent delivery sheaths or catheters to effectuate recapture of a partially deployed stented prosthetic heart valve;

FIG. 3 is a simplified cross-sectional view of a transcatheter heart valve repair system in accordance with principles of the present disclosure, including a delivery device and a stented prosthetic heart valve;

FIG. 5A is a side view of a tube portion of a delivery capsule component of the delivery device of FIG. 2, including a distal zone in a normal or relaxed state;

FIG. 5B is a side view of the tube of FIG. 5A and including the distal zone in a flared state and an intermediate zone in a flexed condition;

FIG. 11A is a cross-sectional view of a portion of a heart valve replacement system in accordance with the present disclosure, including the delivery device of FIG. 9 loaded with the prosthetic heart valve of FIG. 4B;

FIG. 11B is a side view of the heart valve replacement system of FIG. 11A;

FIGS. 12A-16 illustrate use of the system of FIG. 3 in delivering a stented prosthetic heart valve to an implantation site, including partial deployment and recapturing of the prosthesis;

DETAILED DESCRIPTION

Figure 2A:
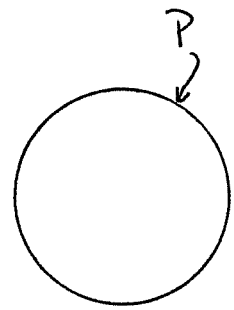
FIGS. 2A-2D are simplified end views of a stent frame of a stented prosthetic heart valve undergoing recapture and experiencing infolding.
Figure 2B:
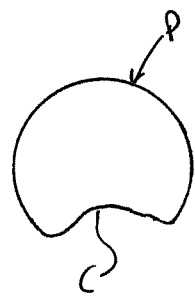
Figure 2C:
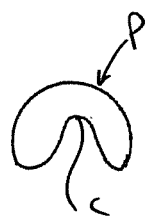
Figure 2D:
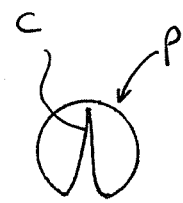

Current transcatheter valve delivery systems do not have the capability of transcatheter valve re-positioning in the antegrade or retrograde directions after partial deployment. The delivery devices and systems of the present disclosure overcome these problems, and permit the clinician to partially deploy the transcatheter valve, and prior to full release, recapture and reposition or remove it. In general terms, the devices function by reducing the peak forces required to recapture the stented prosthesis, while at the same time increasing the axial strength and buckling resistance of the device component utilized to effectuate recapture.

With the above in mind, FIG. 3 illustrates, in simplified form, one embodiment of a heart valve repair system 18. The system 18 generally includes a delivery device 20 and a stented prosthetic heart valve 22. As a point of reference, FIG. 3 illustrates a loaded state of the system 18 in which the stented heart valve prosthesis 22 is compressed and loaded within the delivery device 20. The delivery device 20 includes an inner shaft assembly 24, a sheath assembly 26, a delivery capsule 28, and a handle 30 (referenced generally). Details on the various components are provided below. In general terms, however, the inner shaft assembly 24 is slidably received within a portion of the sheath assembly 26 and the delivery capsule 28, and is configured for releasable coupling with the prosthesis 22. The delivery capsule 28 extends distally from, or is provided as part of, the sheath assembly 26, and is configured to permit partial and complete deployment of the prosthesis 22 from the loaded state of the system 18 (e.g., FIG. 3), as well as to recapture the prosthesis 22 following partial deployment. By incorporating a shape memory (e.g., Nitinol) structure into the delivery capsule 28, a portion of the delivery capsule 28 is allowed to expand circumferentially or flare at a distal end thereof when encountering the outward radial forces (or resistance to radial compression) of the transcatheter valve prosthesis 22 during deployment and recapture. The expanded structure reduces the peak forces required to collapse the cells of a stent frame of the prosthesis 22 by redistributing the potential energy along a length of the expanded flare. In some embodiments, the delivery capsule 28 further incorporate features that impart non-kinking flexibility. This flexible or articulatable region allows the delivery capsule 28 to orient itself in, for example, the aortic arch, thereby reducing the retraction force required for recapturing the prosthesis 22 along a bend.

As referred to herein, stented transcatheter prosthetic heart valves useful with and/or as part of the various systems, devices, and methods of the present disclosure may assume a wide variety of different configurations, such as a bioprosthetic heart valve having tissue leaflets or a synthetic heart valve having polymeric, metallic, or tissue-engineered leaflets, and can be specifically configured for replacing any heart valve. Thus, the stented prosthetic heart valve useful with the systems, devices, and methods of the present disclosure can be generally used for replacement of a native aortic, mitral, pulmonic, or tricuspid valve, for use as a venous valve, or to replace a failed bioprosthesis, such as in the area of an aortic valve or mitral valve, for example.

In general terms, the stented prosthetic heart valves of the present disclosure include a stent or stent frame maintaining a valve structure (tissue or synthetic), with the stent having a normal, expanded arrangement and collapsible to a compressed arrangement for loading within a delivery device. The stent is normally constructed to self-deploy or self-expand when released from the delivery device. For example, the stented prosthetic heart valve useful with the present disclosure can be a prosthetic valve sold under the trade name CoreValve® available from Medtronic CoreValve, LLC. Other non-limiting examples of transcatheter heart valve prostheses useful with systems, devices, and methods of the present disclosure are described in U.S. Publication Nos. 2006/0265056; 2007/0239266; and 2007/0239269, the teachings of each which are incorporated herein by reference. The stents or stent frames are support structures that comprise a number of struts or wire portions arranged relative to each other to provide a desired compressibility and strength to the prosthetic heart valve. In general terms, the stents or stent frames of the present disclosure are generally tubular support structures having an internal area in which valve structure leaflets will be secured. The leaflets can be formed from a variety of materials, such as autologous tissue, xenograph material, or synthetics as are known in the art. The leaflets may be provided as a homogenous, biological valve structure, such as porcine, bovine, or equine valves. Alternatively, the leaflets can be provided independent of one another (e.g., bovine or equine pericardial leaflets) and subsequently assembled to the support structure of the stent frame. In another alternative, the stent frame and leaflets can be fabricated at the same time, such as may be accomplished using high-strength nano-manufactured NiTi films produced at Advance BioProsthetic Surfaces (ABPS), for example. The stent frame support structures are generally configured to accommodate at least two (typically three) leaflets; however, stented prosthetic heart valves of the types described herein can incorporate more or less than three leaflets.

Some embodiments of the stent frames can be a series of wires or wire segments arranged such that they are capable of self-transitioning from the compressed or collapsed arrangement to the normal, radially expanded arrangement. In some constructions, a number of individual wires comprising the stent frame support structure can be formed of a metal or other material. These wires are arranged in such a way that the stent frame support structure allows for folding or compressing or crimping to the compressed arrangement in which the internal diameter is smaller than the internal diameter when in the normal, expanded arrangement. In the compressed arrangement, such a stent frame support structure with attached valve leaflets can be mounted onto a delivery device. The stent frame support structures are configured so that they can be changed to their normal, expanded arrangement when desired, such as by the relative movement of one or more outer sheaths relative to a length of the stent frame.

The wires of these stent frame support structures in embodiments of the present disclosure can be formed from a shape memory material such as a nickel titanium alloy (e.g., Nitinol™). With this material, the support structure is self-expandable from the compressed arrangement to the normal, expanded arrangement, such as by the application of heat, energy, and the like, or by the removal of external forces (e.g., compressive forces). This stent frame support structure can also be compressed and re-expanded multiple times without damaging the structure of the stent frame. In addition, the stent frame support structure of such an embodiment may be laser-cut from a single piece of material or may be assembled from a number of different components. For these types of stent frame structures, one example of a delivery device that can be used includes a catheter with a retractable sheath that covers the stent frame until it is to be deployed, at which point the sheath can be retracted to allow the stent frame to self-expand. Further details of such embodiments are discussed below.

Figure 4A:
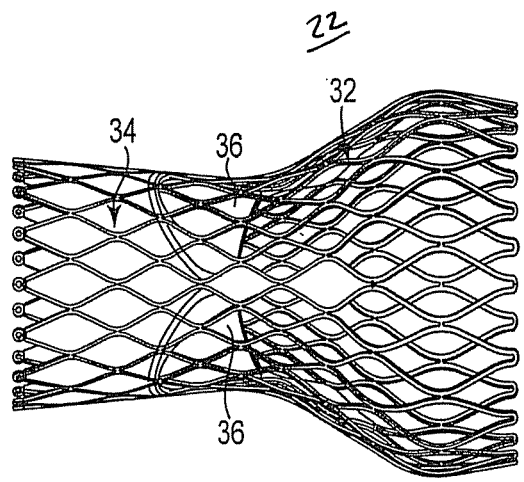
FIG. 4A is a side view of a stented prosthetic heart valve useful with systems and methods of the present disclosure and in a normal, expanded arrangement.
Figure 4B:
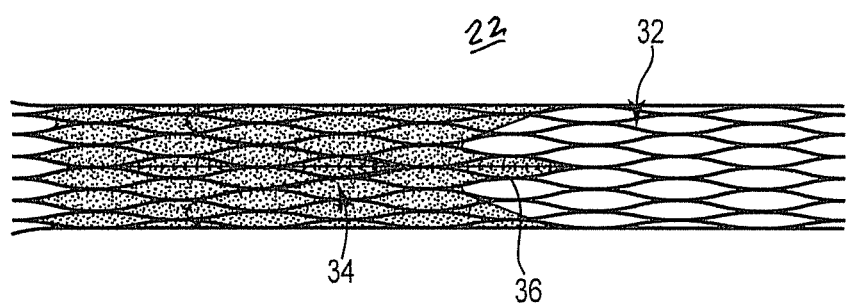
FIG. 4B is a side view of the prosthetic heart valve of FIG. 4A in a compressed arrangement.

With the above understanding in mind, one non-limiting example of the stented prosthetic heart valve 22 useful with systems, devices, and methods of the present disclosure is illustrated in FIG. 4A. As a point of reference, the prosthetic heart valve 22 is shown in a normal or expanded arrangement in the view of FIG. 4A; FIG. 4B illustrates the prosthetic heart valve 22 in a compressed arrangement (e.g., when compressively retained within an outer catheter or sheath). The prosthetic heart valve 22 includes a stent or stent frame 32 and a valve structure 34. The stent frame 32 can assume any of the forms described above, and is generally constructed so as to be self-expandable from the compressed arrangement (FIG. 4B) to the normal, expanded arrangement (FIG. 4A). In other embodiments, the stent frame 32 is expandable to the expanded arrangement by a separate device (e.g., a balloon internally located within the stent frame 32). The valve structure 34 is assembled to the stent frame 32 and provides two or more (typically three) leaflets 36. The valve structure 34 can assume any of the forms described above, and can be assembled to the stent frame 32 in various manners, such as by sewing the valve structure 34 to one or more of the wire segments defined by the stent frame 32.

With the but one acceptable construction of FIGS. 4A and 4B, the prosthetic heart valve 22 is configured for replacing or repairing an aortic valve. Alternatively, other shapes are also envisioned, adapted to the specific anatomy of the valve to be repaired (e.g., stented prosthetic heart valves in accordance with the present disclosure can be shaped and/or sized for replacing a native mitral, pulmonic, or tricuspid valve). With the one construction of FIGS. 4A and 4B, the valve structure 34 extends less than the entire length of the stent frame 32, but in other embodiments can extend along an entirety, or a near entirety, of a length of the stent frame 32. A wide variety of other constructions are also acceptable and within the scope of the present disclosure. For example, the stent frame 32 can have a more cylindrical shape in the normal, expanded arrangement.

With embodiments incorporating the self-expanding stent frame 32, the prosthesis 22 (and in particular the stent frame 32) is conventionally configured to generate a high radially expansive force (alternatively referred to as a chronic outward force) when forced to the compressed arrangement of FIG. 4B, and exhibit high resistance to radial compression (alternatively referred to as a radial resistive force or force required to compress the stent frame 32) once in the expanded arrangement of FIG. 4A. As described below, these chronic outward forces radial resistive forces render recapturing of the prosthesis 22 in a partially expanded arrangement exceedingly difficult. As a point of reference, the chronic outward force/radial resistive force characteristics of the prosthesis 22 can be determined by testing. In particular using an iris-type radial expansion force gauge, such as an MSI RX600 or RX650 available from Machine Solutions, Inc., of Flagstaff, Ariz. The stent frame 32 is loaded in a natural, relaxed, or expanded arrangement, and the force gauge operated to compress the stent frame 32 down to the minimum contracted arrangement. During compression, the force required the compress the stent frame 32 is monitored and logged as a function of frame diameter to provide radial resistive force data. After compression to the minimum diameter representing the minimum diameter when loaded to the delivery device 20 (FIG. 3), the stent frame 32 is allowed to expand to the starting, unconstrained diameter. In accordance with the compression step described above, the expansion force is monitored by the force gauge and logged as a function of stent frame diameter to provided chronic outward force data. Using these methodologies, in some embodiments, the stent frame 32 has a maximum radial resistive force of at least 25 lbf. For example, the stent frame 32 of 26 mm and 29 mm CoreValve™ percutaneous aortic valves were tested in accordance with the above protocols at a temperature of approximately 37° C. and constant strain rate of 0.5 mm/sec and found, when compressed to a diameter of 5.5 mm, to have a maximum or peak radial resistive force in excess of 25 lbf. In fact, the 26 mm and 29 mm CoreValve percutaneous aortic valve stent frames exhibited radial resistive forces approaching and even exceeding 30 lbf at the 5.5 mm crimped diameter. Even with these elevated opening or radial resistive forces, it has surprisingly been found that by incorporating the delivery capsule 28 (FIG. 3) as described below, recapturing of the prosthesis 22 is consistently achieved, even in the presence of a tortuous implantation site (such as when curved along the aortic arch).

Returning to FIG. 3, the delivery capsule 28 is a beneficial feature of the device 20, and thus is initially described in detail below. The remaining components of the delivery device 20 (e.g., the inner shaft assembly 24, the sheath assembly 26, and the handle 30) can assume a wide variety of forms now known or in the future developed. In general terms, however, the delivery capsule 28 is mounted to a sheath or shaft 40 of the sheath assembly 26.

Figure 5C:
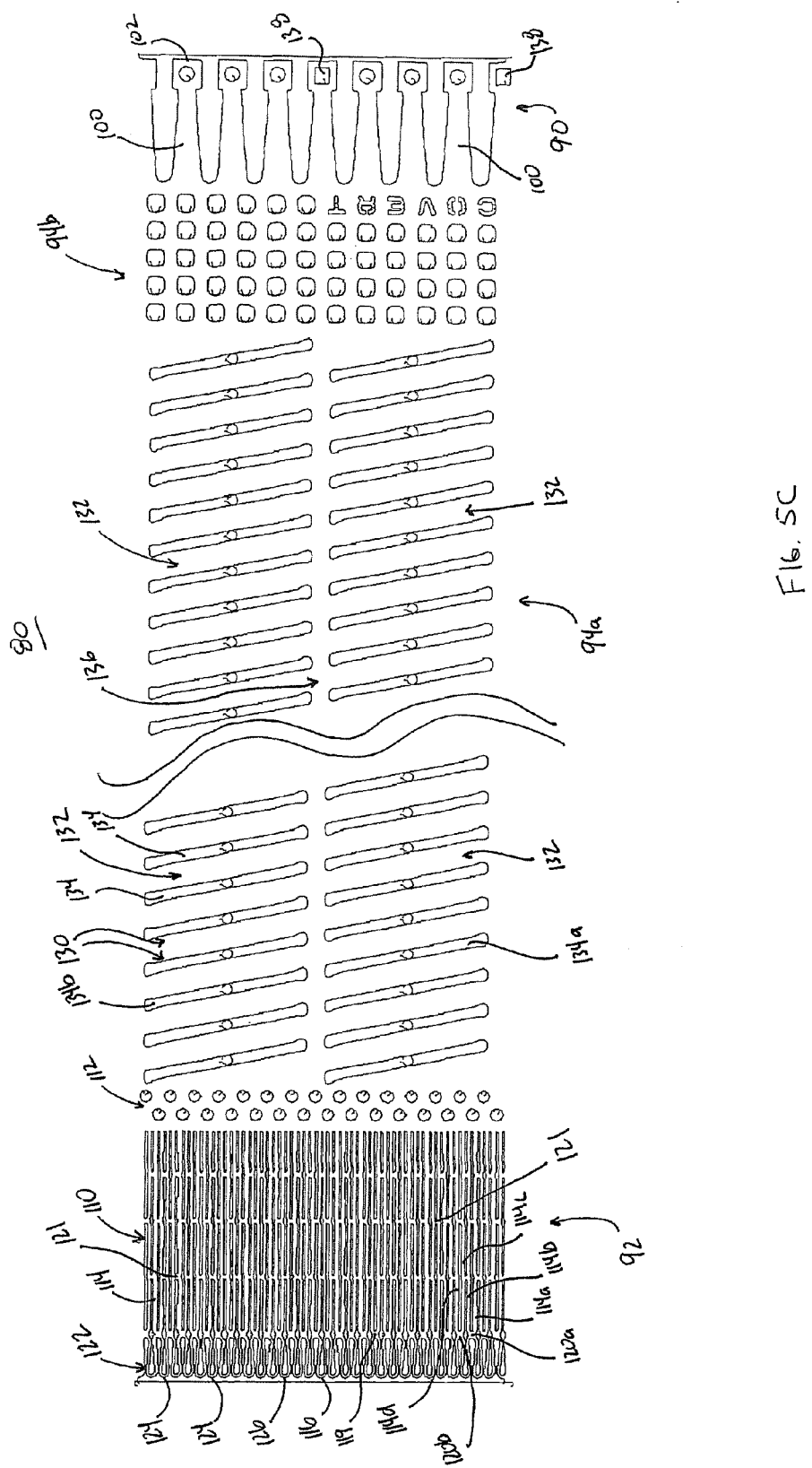
FIG. 5C is an enlarged two-dimensional or unwrapped representation of the tube of FIG. 5A.

The delivery capsule 28 is generally formed as a tubular sleeve and includes a cut tube (e.g., a laser cut tube) embedded or encapsulated within a polymer. FIGS. 5A and 5B illustrate one embodiment of a laser cut tube 80 useful with the delivery capsule 28 of FIG. 3. FIG. 5C is a two-dimensional or "unwrapped" representation of the tube 80, illustrating the cut pattern in greater detail. Various expansion and articulation features imparted into the laser cut tube 80 are described below, with a shape memory characteristic of the tube 80 facilitating repeatable transitioning of the delivery capsule 28 between a normal or contracted state of FIG. 5A to a flared or expanded state of FIG. 5B. In this regard, various shape memory materials can be used for the tube 80, such as a steel, polymers, etc. In some embodiments, the tube 80 is a Nitinol material, and in particular a Nitinol super elastic material. For example, in some non-limiting embodiments, the tube 80 is a Nitinol super elastic material composition per ASTM 2063-05 and ASTM F 2063-00, composed of 55.94% Nitinol, 227 ppm oxygen, 9 ppm hydrogen, 280 ppm carbon, and the balance of titanium. Other materials are also acceptable. Similarly, the encapsulating polymer can assume variety of forms exhibiting biocompatibility, as well as bonding compatibility with a material of the sheath 40 (FIG. 3). For example, the encapsulating polymer can be Pebax. Other materials useful as the encapsulating polymer are described below.

The delivery capsule 28, and in particular the tube 80, defines or is defined by a proximal zone 90, a distal zone 92, and one or more intermediate zones 94. The proximal zone 90 is configured for mounting to a distal end of the sheath 40 (FIG. 3), and in some constructions includes a plurality of circumferentially-spaced fingers 100, each terminating a proximal end 102. In some constructions, the proximal end 102 of each of the fingers 100 can have an enlarged width as shown. Regardless, the spaced fingers 100 are readily interposed within (alternatively over) the distal end of the sheath 40 so as to facilitate attachment thereto (e.g., adhesive bond, heated fusing, etc.).

The distal zone 92 is configured to provide a circumferentially flaring feature, transitioning from the normal or non-flared state of FIG. 5A to the flared state of FIG. 5B when subjected to an expansion force, and self-transitioning back toward the normal state when the expansion force is removed. In this regard, the distal zone 92 is specifically constructed so as to reduce the force required to recapture a partially-deployed transcatheter valve prosthesis, while increasing the axial strength and buckling resistance of the delivery capsule 28 (FIG. 3). For example, in some embodiments, the tube 80 at the distal zone 92 includes a lattice or scaffolding segment 110 and a base or collar segment 112. The lattice segment 110 includes a plurality of generally longitudinally extending splines or struts 114 extending distally from the base 112 to a distal end 116. In the one embodiment of FIGS. 5A-5C, the splines 114 are oriented to extend parallel with the central axis of the tube 80. For example, with respect to first and second splines 114a, 114b identified in FIGS. 5A and 5C, extension of the spines 114a, 114b from the base 112 are parallel with one another and with the central axis. Alternatively, in the normal state of FIG. 5A, the splines 114 can deviate from a true longitudinal orientation (relative to a central axis of the tube 80). Regardless, the splines 114 are each deflectable or pivotable relative to the base 112, pivoting or deflecting a pivot point (identified at 118 in FIGS. 5A and 5C) or point of departure from the base 112. With this construction, then, transitioning between the normal and flared states includes each of the splines 114 pivoting relative to the base 112 at the corresponding pivot point 118. As further clarified by a comparison of FIGS. 5A and 5B, an inner diameter defined at the distal end 116 of the distal zone 92 is increased in the flared state (FIG. 5B) as compared to the normal state (FIG. 5A), with the delivery capsule 28 again being constructed to naturally assume (via shape memory) the normal or relaxed state.

Circumferential stability of the lattice segment 110 is enhanced by interconnecting adjacent pairs of the splines 114 at corresponding distal ends 119. For example, the distal ends 119 of the splines 114a, 114b are connected at a distal bond point 120a; similarly, the distal ends 119 of the splines 114c, 114d are interconnected at a bond point 120b. However, the distal end 119 of the second spline 114b is not directly connected or bonded the distal end 119 of the third spline 114c. Additionally, intermediate bond points 121 are also included between various adjacent splines 114.

Figure 6:
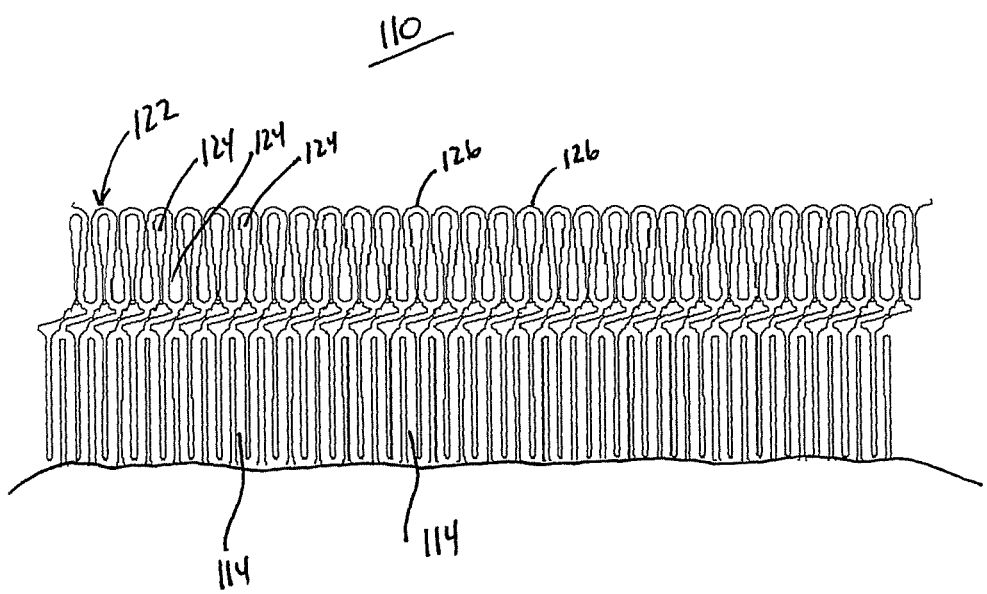
FIG. 6 is an enlarged two-dimensional or unwrapped view of a distal portion of the tube of FIG. 5A.

To promote a desired resistance to circumferential expansion (i.e., resistance to transitioning from the collapsed state to the flared state) and/or inward radial biasing force (i.e., force generated by the shape memory attribute in self-transitioning from the flared state to the contracted or collapsed state), the distal zone 92 can further include an undulating or sinusoidal-like strut 122 that interconnects the distal bond points 120, and thus the distal end 119 of adjacent ones of the splines 114. The undulating strut 122 can be continuous as shown, or can be comprised of discrete strut segments. Regardless, the undulating shape of the strut 122 generates a series of overlapping loops 124 as best shown in FIG. 6. The loops 124 each form a crown 126 at the distal end 116 of the tube 80. The crowns 126 are rounded for atraumatic interface with the prosthetic valve 22 (FIG. 4A). To minimize the propensity for tearing, delamination, and/or catching on the stented heart valve prosthesis 22 (FIG. 4A), a variety of other crown shapes or configurations can be employed. Further, the overlapping nature of the loops 124 renders the strut 122 less resistant to radial expansion (as compared to a resistance of the lattice segment 110). Returning to FIGS. 5A-5C, with embodiments incorporating the continuous strut 122, the distal zone 92 has been found to maintain its expansion properties while increasing its resistance to delamination and tear.

The base or collar segment 112 can be circumferentially more rigid as compared to the lattice segment 110, and provides a more robust resistance to a radially outward force. Thus, the base 112 can include circumferentially-spaced cut-outs 128 as shown, although other configurations are also acceptable.

As indicated above, the tube 80, and thus the delivery capsule 28 (FIG. 3), can include one or more of the intermediate zones 94. With the one embodiment of FIGS. 5A-5C, for example, the delivery capsule 28 includes or defines an intermediate flex zone 94a that is longitudinally disposed between the proximal and distal zones 90, 92. In general terms, the flex zone 94a incorporates features that impart circumferential or radial rigidity, yet permit or promote transverse articulation, designed to give the delivery capsule 28 adequate axial and radial strength to prevent buckling or kinking. For example, in some embodiments, the tube 80 includes, along the intermediate flex zone 94a, a partial coil or helix-like cut pattern 130 that establishes a plurality of generally circumferentially extending coil segments 132. Longitudinally adjacent ones of the coil segments 132 are separated by a cut 134. The cuts 134 are circumferentially discontinuous, extending less than 180°. As such, the first and second cuts 134a, 134b identified in FIG. 5C are helically aligned, but are separated from one another. Thus, the cut pattern 130 establishes one or more longitudinal spines 136. With the construction of FIGS. 5A-5C, two of the spines 136 are formed circumferentially opposite one another (it being understood that only one of the spines 136 is visible in FIGS. 5A and 5B, and that in the flat or unwound representation of FIG. 5C, only one of the spines 136 is readily identifiable).

The discontinuous cuts 134 and the spines 136 generally connect or maintain adjacent ones of the coil segments 132 relative to one another, yet permit transverse articulation. The coil segments 132 can thus articulate from the relatively straight arrangement of FIG. 5A to the articulated or curved orientation reflected in FIG. 5B. Other constructions that promote desired transverse articulation are also envisioned. Bond sites can be added, for example, to decrease an overall thickness of the tube 80 and increase bond strength (to the encapsulating polymer). Increasing the bondable area decreases the amount of movement of the tube 80 within the encapsulating polymer, thereby reducing the potential for delamination. While being flexible for requisite bending or articulation (due to a material strength, thickness, and circumferential width), the spines 136 (in combination with the coil segments 132) provide an enhanced hoop strength attribute to the zone 94a, to constrain the prosthesis 22 (FIG. 4A) in the collapsed arrangement as well as longitudinal stability for distally advancing the delivery capsule 28 over a partially deployed (and radially expanded) prosthesis as described below. Further, the delivery sheath 40 (FIG. 3) can incorporate complimentary spine-like components as described below. With these and other embodiments, the tube 80 can be configured to readily identify a location of the spines 136 to a user. For example, the finger(s) 100 of the proximal zone 90 otherwise aligned with one of the spines 136 can have a unique shape or identifier 138 as shown in FIG. 5C.

The delivery capsule 28 can include additional intermediate zones, such as the second intermediate zone 94b identified in FIGS. 5A-5C. In general terms, the second intermediate zone 94b serves to provide a more robust columnar strength as well as more rigid resistance to radial expansion, and is configured to constrain the stented heart valve prosthesis 22 (FIG. 4A) in or near the collapsed arrangement. Thus, in some constructions, the second intermediate zone 94b consists or forms a plurality of longitudinal and circumferential segments 140, 142 that are interconnected to one another and combine to resist radial expansion.

Figure 5D:
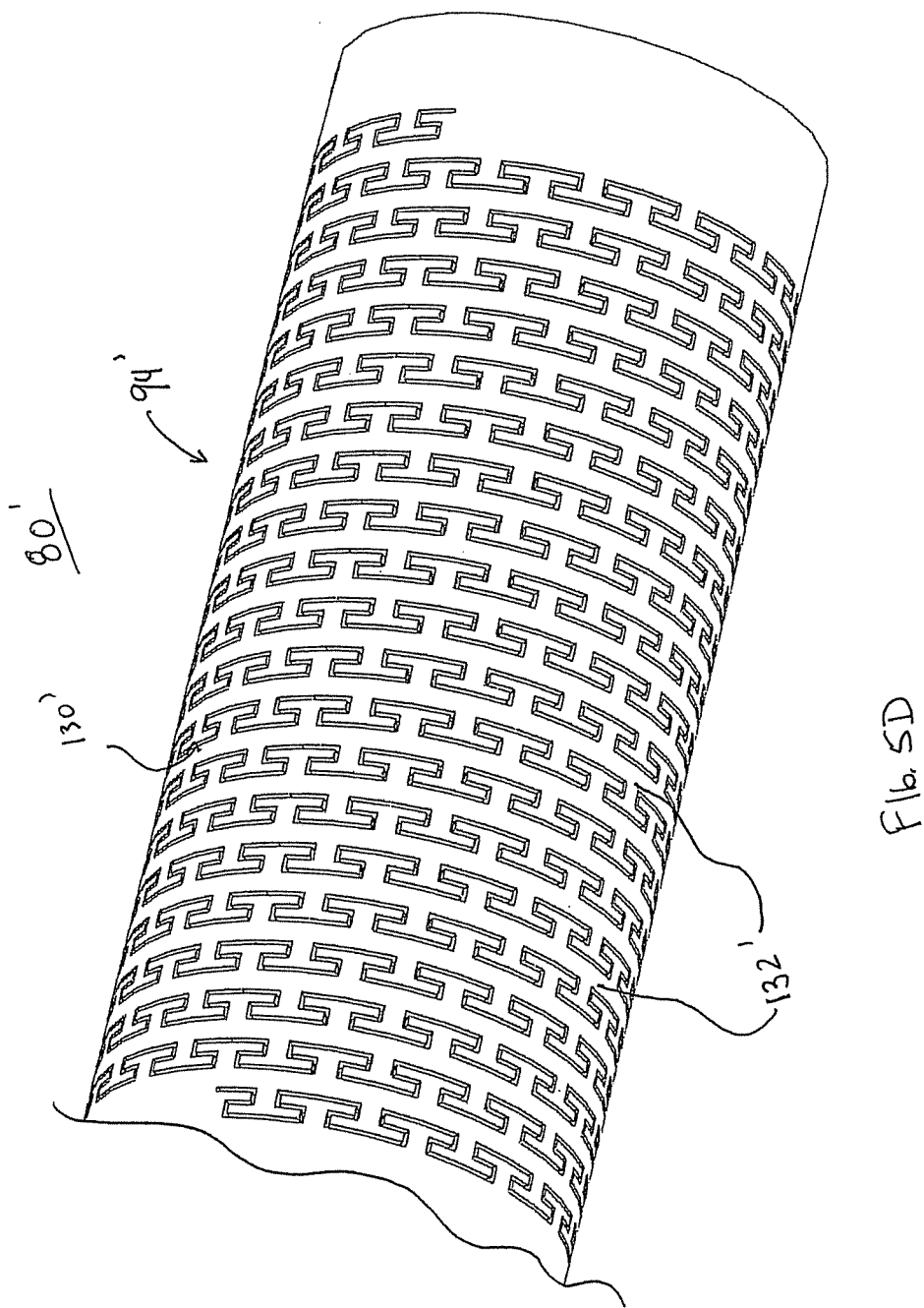
FIG. 5D is a perspective view of a portion of an alternative tube useful with the delivery capsule of FIG. 3.

Other constructions of the flex zone 94 are also acceptable, and in some embodiments, the second intermediate zone 94b can be omitted. For example, while the coil segments 132 are shown as having a uniform pitch, in other embodiments, a variable pitch construction is employed (e.g., a distally increasing pitch). FIG. 5D illustrates a portion of an alternative laser cut tube 80', and in particular a flexible intermediate zone 94' thereof. A cut pattern 130' has a dovetail-like shape, defining segments 132' that can flex or articulate relative to one another when the intermediate zone 94' is subjected to a transverse bending force. The intermediate zone 94' exhibits enhanced columnar strength and is readily flexed.

Figure 7:
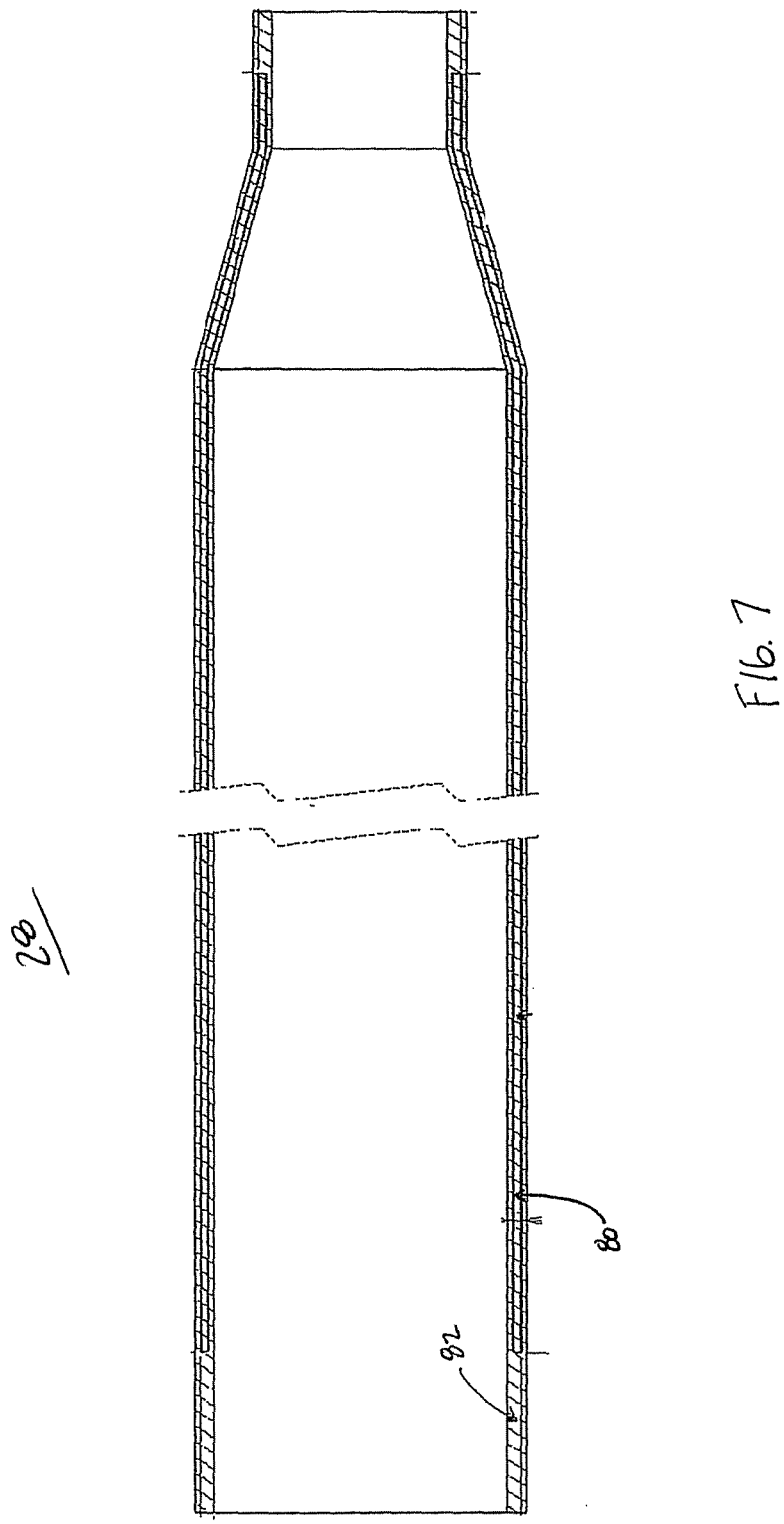
FIG. 7 is a cross-sectional view of the delivery capsule of FIG. 3.

Returning to FIG. 5A, as indicated above, the core of the delivery capsule 28 can be the laser cut tube 80. In some constructions, the tube 80 is initially provided as a Nitinol hypo-tube into which the lattice or scaffolding-like structure(s) are formed. For example, one non-limiting, simplified example of the delivery capsule 28, including the laser cut tube 80 (shown without the cut patterns for ease of illustration) and encapsulating polymer 82, is shown in FIG. 7. In these and other embodiments, the polymer encasement 82 extends distally and proximally beyond the core tube 80. Alternatively, the polymer encasement 82 can terminate at the opposing ends of the tube 80.

Nitinol is employed for the tube 80 due to its ability to recover after experiencing high forces and deformation. Nitinol's mechanical properties allow the cut tube 80 structure to expand and return to its original shape, providing the flared or funnel shape for reduction in retraction forces. Following cutting, the tube 80 can be de-burred by hand filing using a round filing mandrel. Additional processing, such as microblasting, can also be performed. Subsequently, the tube 80 can be rinsed in IPA and placed into a BS acid etch solution (e.g., for one minute). The acid can be heated to 40° C. while ultrasonically vibrated. Additional processing (e.g., electropolishing to remove sharp edges, micro-cracks, reduce wall thickness, etc.), can also be performed.

The polymer encasement 82 can be applied to the laser cut tube 80 in a variety of fashions, for example, dip coating, heat fusing, etc. The materials selected for the polymer encasement 82 can vary. For example, the encasement 82 can be formed by inner and outer liner materials applied to the laser cut tube 80, with the liner material being identical or at least similar in their chemical makeup. The selected liner material(s) exhibit, in some constructions, a balance between high strength, low elastic hysteresis, and lubricity. For example, the liner material(s) can be Elasthane, Pellethane™, Pebax, Grilamide™, etc. In some embodiments, the polymer encasement 82 is a polyblend formulated as a modified thermoplastic polyether urethane. Elasthane™ 80A TPU (available from DSM PTG of Berkeley, Calif. (formerly The Polymer Technology Group)) can be used as the principal component of the polyblend because of its moderate strength, low elastic hysteresis, and history of use in biomedical applications. A siloxane polymer in polyurethane carrier resin can be selected as the other component of this polyblend, to impart lubricity without causing migration or blooming. In some constructions, these two components are melt-blended in a single-screw extruder in 90:10 and 80:20 weight ratios. The resultant polyblends exhibit the same low elastic hysteresis behavior as Elasthane™ 80A TPU when their tubing forms were radially expanded to about 300% for 5 consecutive times. The 90:10 and 80:20 polyblends showed about 190% and 205% higher yield strength than Elasthane™ 80A TPU. The 90:10 and 80:20 polyblends were also found to be about 12% and 53% more lubricious than Elasthane™ 80A TPU. Considering these results, the 80:20 polyblend of Elasthane™ 80A TPU and siloxane masterbatch offers an attractive option to modify a commercially available medical grade polymer, achieving the desired combination of conflicting properties for the polymer encasement 82. It has surprisingly been found through testing that the polymer blend described above has a much higher tear load than the base material. By blending thermoelastomers with a siloxane masterbatch or silicone-containing material, a new material with good elasticity, better lubricity, and higher tear load is achieved and is highly useful for a stented prosthetic heart valve delivery capsule. The base polymers can be SBS, SIBS, thermoelastic polyurethane, polyamide, etc. The ratio of the siloxane masterbatch can be in the range of 5-50%.

Figure 8:
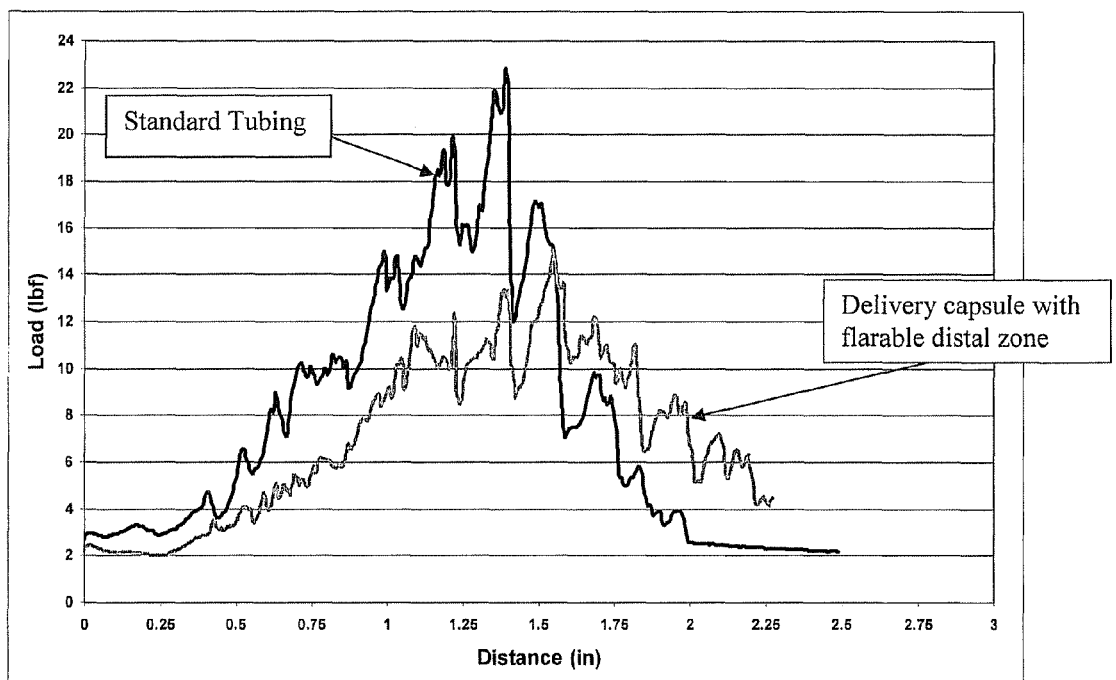
FIG. 8 is a graph comparing retraction forces experienced by a delivery capsule incorporating a flarable distal zone in accordance with principles of the present disclosure as compared to a conventional sheath or catheter.

Returning to FIGS. 5A-5C, by employing the flarable distal zone 92, the delivery capsule 28 redistributes the radial force energy curve, reducing the overall forces for retraction while performing the same amount of work. With the ability to flare, the peak forces necessary to compress the stented heart valve prosthesis 22 (FIG. 4A) is reduced. The funnel or flared shape created by the expanded distal zone 92 also reduces the potential for interference with pillowing tissue and/or skirt material. FIG. 8 is a graph illustrating the force redistribution effectuated by the flarable distal zone 92 as compared to a linear or straight configuration.

Returning to FIG. 3, remaining components of the delivery device 20 can assume a variety of forms appropriate for percutaneously delivering and deploying a stented self-expanding prosthetic heart valve. One embodiment of the delivery device 20 is shown in greater detail in FIG. 9 and includes the inner shaft assembly 24, the sheath assembly 26, the delivery capsule 28, the handle 30, and an optional stability tube 150. The inner shaft assembly 24 can have various constructions appropriate for supporting a stented prosthetic heart valve within the delivery capsule 28. In some embodiments, the inner shaft assembly 24 can include a retention member 200, an intermediate tube 202, and a proximal tube 204. In general terms, the retention member 200 can be akin to a plunger, and incorporates features for retaining the stented prosthetic heart valve within the delivery capsule 28 as described below. The tube 202 connects the retention member 200 to the proximal tube 204, with the proximal tube 204, in turn, coupling the inner shaft assembly 24 with the handle 30. The components 200-204 can combine to define a continuous lumen 206 (referenced generally) sized to slidably receive an auxiliary component such as a guide wire (not shown).

The retention member 200 can include a tip 210, a support tube 212, and a spindle 214. The tip 210 forms or defines a nose cone having a distally tapering outer surface adapted to promote atraumatic contact with bodily tissue. The tip 210 can be fixed or slidable relative to the support tube 212. The support tube 212 extends proximally from the tip 210 and is configured to internally support a compressed, stented prosthetic heart valve generally disposed thereover, and has a length and outer diameter corresponding with dimensional attributes of the selected prosthetic heart valve. The spindle 214 is attached to the support tube 212 opposite the tip 210 (e.g., an adhesive bond), and provides a coupling structure 220 (referenced generally) configured to selectively capture a corresponding feature of the prosthetic heart valve. The coupling structure 220 can assume various forms, and is generally located along an intermediate portion of the inner shaft assembly 24. In some constructions, the coupling structure 220 forms one or more slots sized to slidably receive a corresponding component(s) of the prosthetic heart valve (e.g., a bar or leg segment of the stent frame). Further, the inner shaft assembly 24 can incorporate additional structures and/or mechanisms that assist in temporarily retaining the stented valve (e.g., a tubular sleeve biased over the spindle 214), such as described in U.S. application Ser. No. 12/870,567 entitled "Transcatheter Valve Delivery Systems and Methods" filed Aug. 27, 2010 and the entire teachings of which are incorporated herein by reference. Other releasable coupling arrangements are also acceptable, such as the spindle 214 including one or more fingers sized to be received within corresponding apertures formed by the prosthetic heart valve stent frame (e.g., the prosthetic heart valve stent frame can form wire loops at a proximal end thereof that are received over respective ones of the fingers when compressed within the capsule 28).

The intermediate tube 202 is formed of a flexible polymer material (e.g., PEEK), and is sized to be slidably received within the delivery sheath assembly 26. The proximal tube 204 can include, in some embodiments, a leading portion 222 and a trailing portion 224. The leading portion 222 serves as a transition between the intermediate and proximal tubes 202, 204 and thus in some embodiments is a flexible polymer tubing (e.g., PEEK) having a diameter slightly less than that of the intermediate tube 202. The trailing portion 224 has a more rigid construction, configured for robust assembly with the handle 30 such as a metal hypotube. Other constructions are also envisioned. For example, in other embodiments, the intermediate and proximal tubes 202, 204 are integrally formed as a single, homogenous tube or solid shaft.

The delivery sheath assembly 26 includes the sheath 40 that is connected to the delivery capsule 28, and defines proximal and distal ends 232, 234. With embodiments in which the delivery capsule 28 is considered to be "part" of the delivery sheath assembly 26, then, the delivery capsule 28 defines the distal end 234. The delivery sheath or shaft 40 in some embodiments has a less stiffened construction (as compared to a stiffness of the delivery capsule 28). For example, the delivery sheath 40 can be a polymer tube embedded with a metal braiding. The delivery sheath 40 is constructed to be sufficiently flexible for passage through a patient's vasculature, yet exhibit sufficient longitudinal rigidity to effectuate desired axial movement of the delivery capsule 28. In other words, proximal retraction of the delivery sheath 40 is directly transferred to the capsule 28 and causes a corresponding proximal retraction of the capsule 28. In other embodiments, the delivery sheath 40 is further configured to transmit a rotational force or movement onto the capsule 28.

Figure 10:
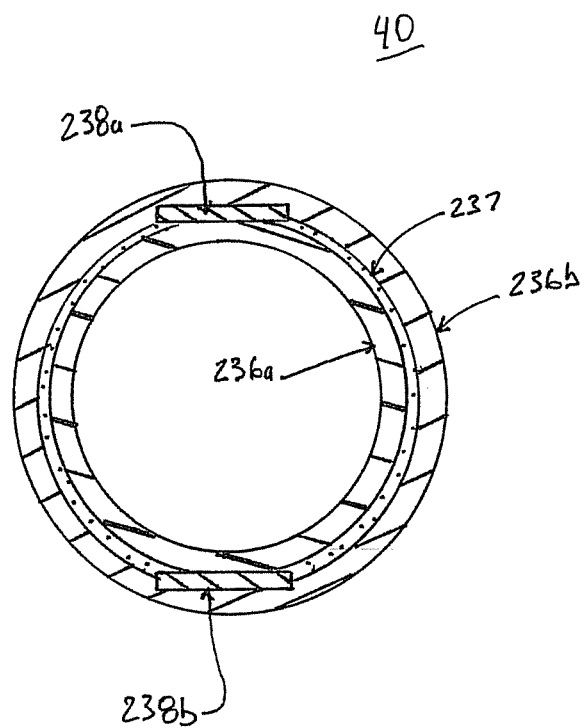
FIG. 10 is a transverse, cross-sectional view of an optional delivery sheath useful with the delivery device of FIG. 9.

In other embodiments, the delivery sheath 40 can be longitudinally reinforced with one or more wires. FIG. 10 is a simplified illustration of the optional delivery sheath 40 construction, and includes, inner and outer tubular layers 236a, 236b encapsulating a braid 237 and circumferentially opposite wires 238a, 238b. The tubular layers 236a, 236b can be formed of identical or differing polymer materials (e.g., the inner tubular layers 236a can be PTFE, nylon, PE TPE, etc., and the outer tubular layer 236b can be EVA, PVC, etc., or other lubricious polymers). The braid 237 can be a conventional metal braid (e.g., stainless steel braiding) and in other embodiments can be omitted. The wires 238a, 238b can be made of a structurally robust material, such as stainless steel, and have the flattened or rectangular shape in some embodiments as illustrated. While other shapes are also acceptable, the flattened construction provides more mass and thus an enhanced ability to "steer" the delivery capsule 28 (FIG. 3) around a bend as described below.

The wires 238a, 238b effectively serve as longitudinal spines. As a point of reference, a major challenge for a delivery system that delivers an aortic valve through percutaneous implantation is the ability to be flexible enough to track through the aortic arch and then have the ability to stretch and compress minimally so that the delivery device can accurately deploy the prosthesis. Within the outer and/or inner shaft(s) 236a, 236b, the longitudinal wires, tapered wires or cables 240 are located 180 degrees apart from each other. Alternatively, two or more of the wires 238 can be included on each side. The resultant sheath 40 can bend back and forth in one direction, but not in the opposite. This characteristic, in turn, forces the delivery capsule 28 (FIG. 9) to rotate so that the wires 238 make the delivery capsule 28 take the path with the least resistance. By having the wires or cables 238 within the shaft(s) 236a, 236b, they are much stronger in tension and much more resistant to compression. Additionally, the distal end of the wires or cables 238 can be tapered to allow for added flexibility. The distal wires 238 can also be pre-shaped to "point" the delivery capsule 28 in the correct direction for tracking over the arch, effectively causing the delivery capsule 28 to rotate to a desired orientation as the delivery capsule 28 and sheath 40 successively traverse the aortic arch. In some embodiments, if the "preshaping" imparted by the wires 238 limits an ability of the delivery sheath 40 to properly track through the expected anatomy (e.g., the descending aorta), the optional stability tube 150 (FIG. 9) can be provided. The stability tube 150 is a polymer-based tube or catheter that is slidably disposed over the sheath 40. Where provided, the stability tube 150 renders the delivery sheath 40 straightened; once the delivery sheath 40 has been advanced to the anatomical location where bending is desired, the stability tube 150 is retracted, permitting the sheath 40 to more readily bend. Alternatively, the wires or spines 238 can be omitted.

Returning to FIG. 9, the handle 30 generally includes a housing 240 and one or more actuator mechanisms 242 (referenced generally). The housing 240 maintains the actuator mechanism(s) 242, with the handle 30 configured to facilitate sliding movement of the delivery sheath assembly 26 relative to the optional stability tube 150 and the inner shaft assembly 24, as well as the stability tube 150 relative to the inner shaft assembly 24 and the delivery sheath assembly 26. The housing 240 can have any shape or size appropriate for convenient handling by a user. In one simplified construction, a first, deployment actuator mechanism 242a includes a user interface or actuator 244 slidably retained by the housing 240 and coupled to a delivery sheath connector body 246. The proximal end 232 of the delivery sheath assembly 26 is connected to the delivery sheath connector body 246. The inner shaft assembly 24, and in particular the proximal tube 204, is slidably received within a passage 248 (referenced generally) of the delivery sheath connector body 246, and is rigidly coupled to the housing 240. A second, stability tube actuator mechanism 242b (referenced generally) similarly includes a user interface or actuator 250 moveably maintained by the housing 240 and coupled to the stability tube 150 via one or more bodies (not shown) facilitating movement of the stability tube 150 with operation of the stability actuator 250. With this but one acceptable construction, the deployment actuator 244 can be operated to effectuate axial movement of the delivery sheath assembly 26 relative to the stability tube 150 and the inner shaft assembly 24. Similarly, the stability actuator 250 can be manipulated to axially slide the stability tube 150 relative to the inner shaft assembly 24 and the delivery sheath assembly 26. In other embodiments, the handle 30 can have a more simplified form, such as when the stability tube 150 is omitted.

The delivery system 18 is operable to deliver or implant the stented heart valve prosthesis 22 (FIG. 4A) as described below. FIGS. 11A and 11B illustrate the delivery device 20 loaded with the stented heart valve prosthesis 22 prior to deployment. In particular, and as best shown in FIG. 11A, the stented heart valve prosthesis 22 is connected or crimped to the inner shaft assembly 24 via the spindle 214, and is radially constrained to the compressed arrangement within the delivery capsule 28. In some constructions, a majority of the prosthesis 22 is within the intermediate zone 94 of the delivery capsule 28. As a point of reference, the intermediate zone 94 has an increased resistance to radial expansion (as compared to a resistance along the distal zone 92), such that when the prosthesis 22 is located within the intermediate zone 94, the prosthesis 22 is held in the compressed arrangement. The optional stability tube 150 is positioned proximal the distal capsule 28.

Figure 12C:
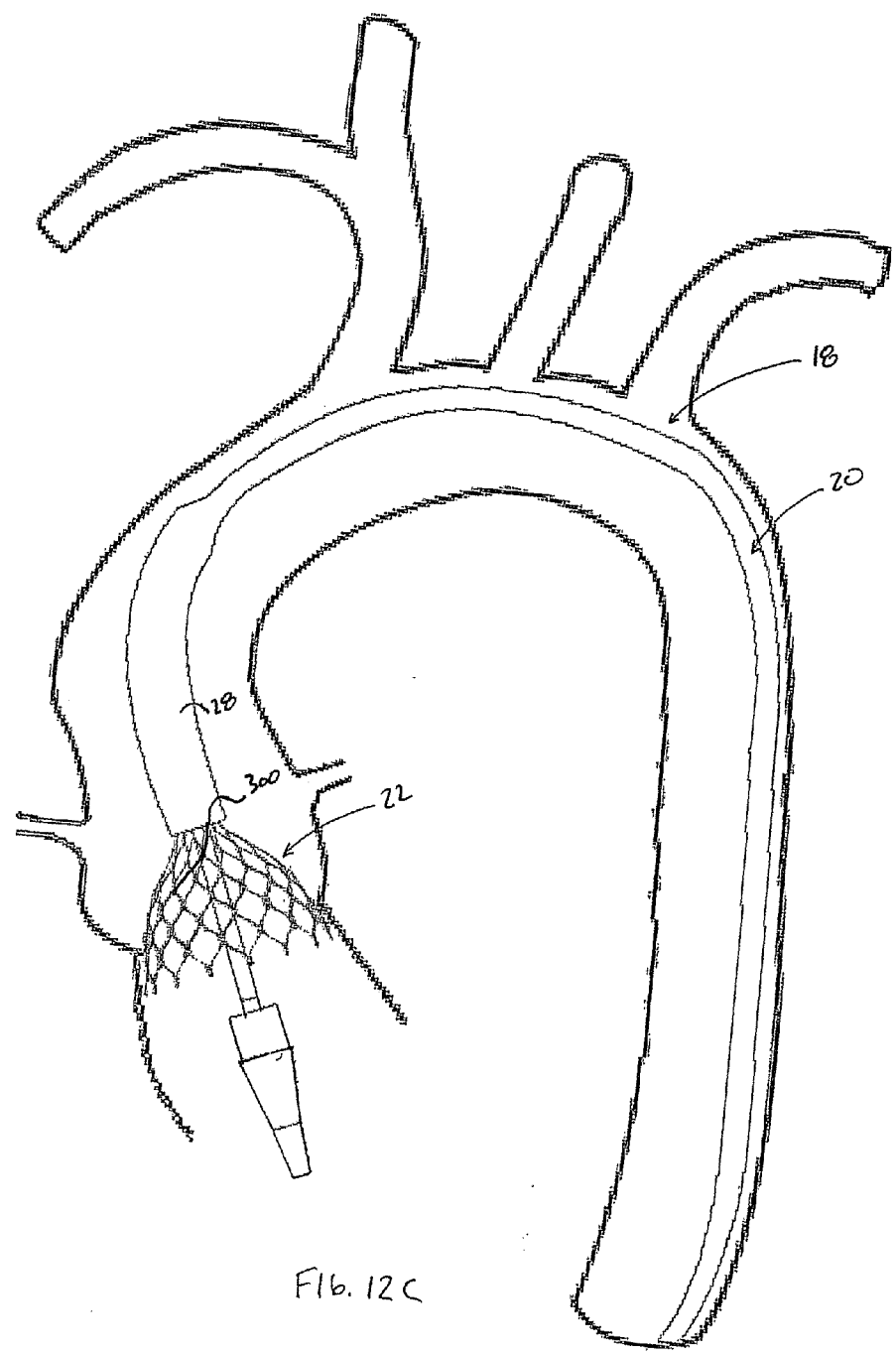

The loaded delivery device 20 can then be used to percutaneously deliver the prosthetic heart valve 22 to an implantation site, such as a defective heart valve. For example, the delivery device 20 is manipulated to advance the compressed prosthetic heart valve 22 toward the implantation target site in a retrograde manner through a cut-down to the femoral artery, into the patient's descending aorta. The delivery device 20 is then advanced, under fluoroscopic guidance, over the aortic arch, through the ascending aorta, and approximately midway across the defective aortic valve (for an aortic valve replacement procedure). Once positioning of the delivery device 20 is estimated, the delivery capsule 28 (and the sheath 40) are partially retracted (proximally) relative to the prosthesis 22 as generally reflected in FIGS. 12A and 12B. As shown, a distal region 300 of the prosthesis 22 is thus exteriorly "exposed" relative to the delivery capsule 28, and is allowed to self-expand. FIG. 12C illustrates the system 18 percutaneously directed to a native valve and the delivery device 20 in a partially retracted state; as shown, the prosthetic heart valve 22 is partially deployed or expanded, yet remains secured to the delivery device 20.

In FIGS. 13A and 13B, proximal retraction of the delivery capsule 28/sheath 40 continues, with an increased length of the prosthesis distal region 300 being exposed and thus self-expanded toward the expanded arrangement. In the state of FIGS. 13A and 13B, however, at least a proximal segment 302 of the prosthesis 22 remains within the confines of the delivery capsule 28, and thus coupled to the delivery device 20. In this partially deployed state, a substantial portion (e.g., 90%) of the stented prosthetic heart valve 22 has self-expanded toward the expanded condition.

In the stage of partial deployment of FIGS. 13A and 13B (or any other sequentially prior stage of deployment), the clinician can perform desired evaluations of the prosthesis 22 relative to the implantation site. Notably, a substantial majority of the prosthetic 22 is expanded, including, for example, the inflow region and at least a portion of the outflow region. In the event the clinician believes, based upon the above evaluation, that the prosthesis 22 should be repositioned relative to the implantation site, the prosthesis 22 must first be contracted or "resheathed". As shown in FIGS. 14A and 14B, the delivery capsule 28/sheath 40 is advanced distally relative to the inner shaft assembly 24, and thus relative to the stented heart valve prosthesis 22. The distal zone 92 of the capsule 28 interfaces with an exterior of the prosthesis 22, and, in response, flares and expands. This action reduces the force imparted upon the stented heart valve prosthesis 22, thus lessening the likelihood of tearing or other damaging interaction. However, column strength for resheathing is maintained. In FIGS. 15A and 15B, distal movement of the delivery capsule 28/sheath 40 continues until the stented heart valve prosthesis 22 is fully resheathed within the delivery capsule 28. The delivery capsule 28 may slightly expand radially; however, the prosthesis 22 is forced back to approximately the initial, collapsed arrangement (of FIGS. 12A and 12B). In accordance with embodiments of the present disclosure, recapture of the prosthesis 22 is accomplished using the same components of the delivery device 20 otherwise employed during prosthesis deployment. In other words, systems, devices, and methods of the present disclosure do not require any additional moving components to effectuate recapture in some embodiments. Instead, the same actuator operated during deployment is operated, in reverse fashion, to accomplish recapture.

Figure 16:
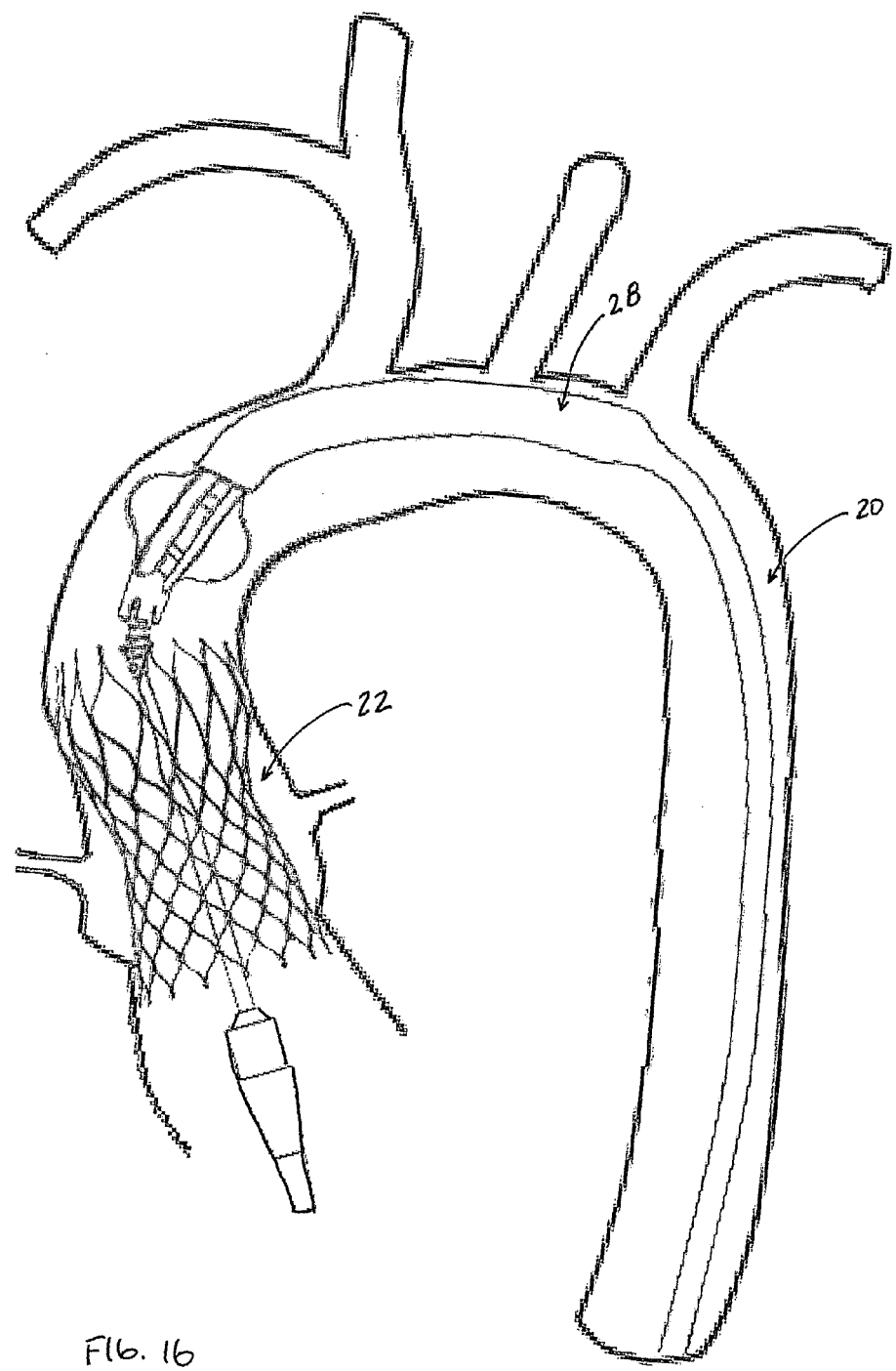

Once resheathed or recaptured, the system 18 can be repositioned relative to the implantation site, and the process repeated until the clinician is comfortable with the achieved positioning. In this regard, because the distal zone 92 has self-transitioned back toward the normal or unflared state, the delivery capsule 28 has returned to a relatively low profile and thus is readily moved or "re-crossed" relative to the native valve. As a point of reference, were the distal zone 92 to remain in the flared state, the corresponding elevated diameter may render re-crossing of the native valve difficult. Once properly positioned, the stented prosthetic heart valve 22 is fully released from the delivery device 20 by retracting the delivery capsule proximally beyond the prosthesis 22. FIG. 16 reflects that the released prosthetic heart valve 22 is now implanted to the native valve. Alternatively, the resheathed stented heart valve prosthesis 22 can be removed from the patient.

As a point of reference, there needs to be a balance between the length of the flared distal zone 92 (FIG. 5B) and the reliability of the delivery capsule 28 because resheathing or recapture would usually be done over the arch of the aorta, and a flare that is too long has a high chance of buckling when bent during recapture. To reduce the likelihood of buckling, the articulating or flexing section or zone 94a (FIG. 5B) is optionally provided just behind the distal flarable zone 92. By way of further explanation, to recapture the prosthetic heart valve 22, the prosthesis 22 must go from an expanded or natural arrangement to a collapsed arrangement over a given distance. The present disclosure envisions that in some embodiments, the partially deployed state entails two-thirds of the length of the prosthesis 22 being deployed. In order to reduce the force required of the delivery capsule 28 to effectuate recapture, the distance of interface between the prosthesis 22 and the delivery capsule 28 can be increased; this is accomplished by the flarable distal zone 92. It has been surprisingly found through testing that the delivery capsule 28 as described above will successfully recapture an expanded stented prosthetic heart valve having a maximum radial resistive force of at least 25 lbf, and recover to its original, normal size when the outward radial force of the prosthesis 22 is removed (e.g., when the flarable distal zone 92 is advanced distal the prosthesis 22) thereby facilitating ready "re-crossing" of the native valve. These same valves were found to not experience infolding due to the distribution of work to collapse the stent frame cells over a greater length and minimization of the radial crimping force. Also, with the high radial resistive force prosthetic valves described above, the delivery device 20 will experience forces on the order of 15-40 lbs. when recapturing. The delivery capsules of the present disclosure were surprisingly found to not buckle under these conditions due, at least in part, to their high columnar strength (e.g., the spines 136 (FIG. 5C)).

Figure 17A:
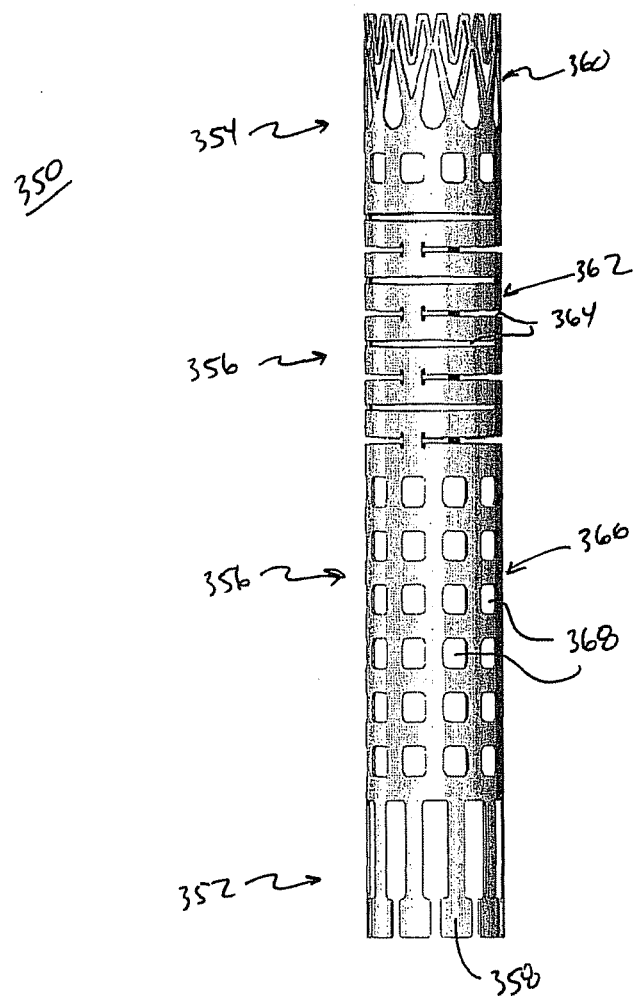
FIG. 17A is a side view of alternative tube useful with the delivery capsule component of the device of FIG. 3 and in a natural or unflared state.
Figure 17B:
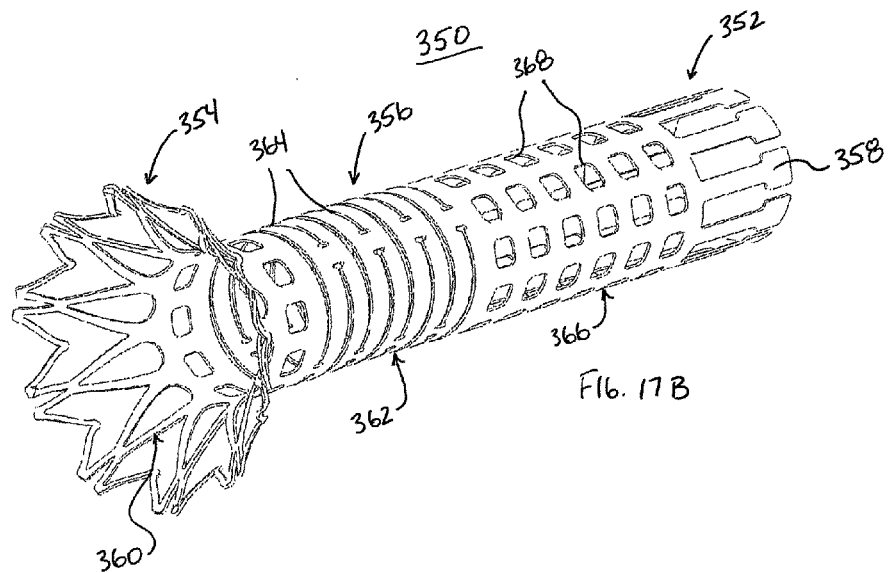
FIG. 17B is a perspective view of the tube of FIG. 17A in a flared state.
Figure 17C:
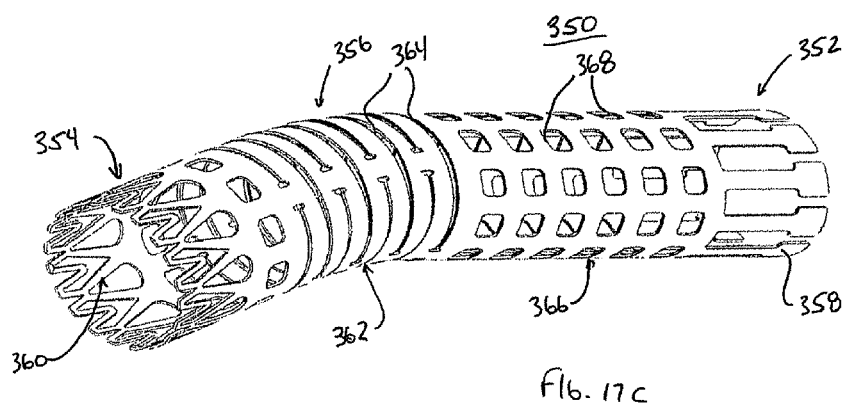
FIG. 17C is a perspective view of the tube of FIG. 17A in an articulated or flexed orientation.

The delivery capsule 28 described above, and in particular the laser cut tube 80, is but one acceptable construction in accordance with principles of the present disclosure. For example, FIGS. 17A-17C illustrate an alternative laser cut tube 350 useful with the delivery capsule 28 (FIG. 3) described above. The tube 350 is formed of a shape memory material (e.g., NiTi), and is cut to define a proximal zone 352, a distal flarable zone 354 and one or more intermediate zones 356. The proximal zone 352 is akin to the proximal zone 90 (FIG. 5A) described above, and can form fingers 358 that facilitate attachment to the delivery sheath 40 (FIG. 3). The distal zone 354 defines a lattice region 360 that will flare from the normal state of FIG. 17A to the flared state of FIG. 17B in response to a radially expansive force (such as when the distal zone 354 is advanced over an expanded portion of a stented prosthetic heart valve). Upon removal of the radially expansive force, the distal zone 354 self-transitions back toward the normal state. Finally, the intermediate zones 356 includes an articulating region 362 defined by circumferential cuts 364, and a support region 366 having a plurality of spaced cut-outs 368. The articulating region 362 is articulatably or deflectable as shown in FIG. 17C, while the support region 366 provides columnar strength and more overt resistance to radial expansion. When employed as part of the delivery capsule 28 (e.g., encapsulated within a polymer and attached to the delivery sheath 40), the tube 350 operates in a manner akin to previous descriptions.

Figure 9:
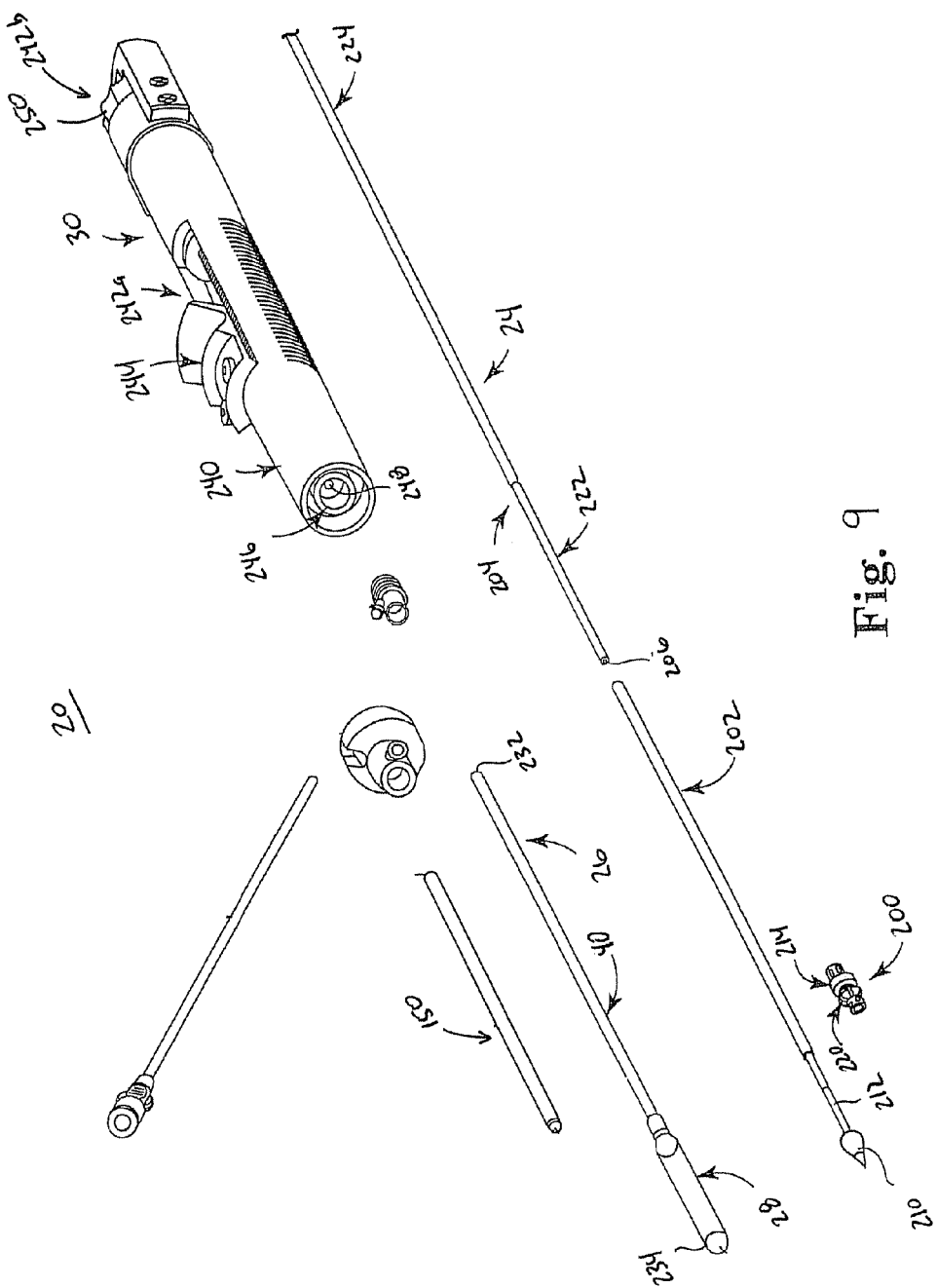
FIG. 9 is an exploded view of a delivery device useful with the system of FIG. 3.
Figure 18A:
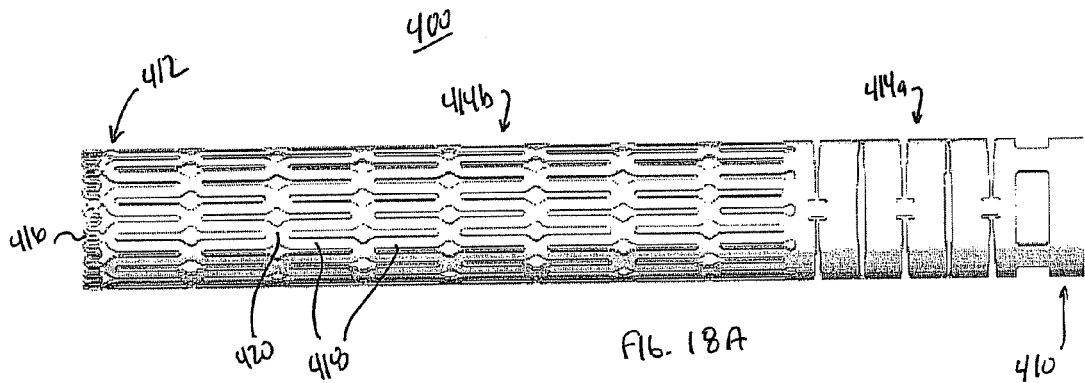
FIG. 18A is a side view of another tube useful with the delivery capsule of FIG. 3 and in a normal or unflared state.
Figure 18B:
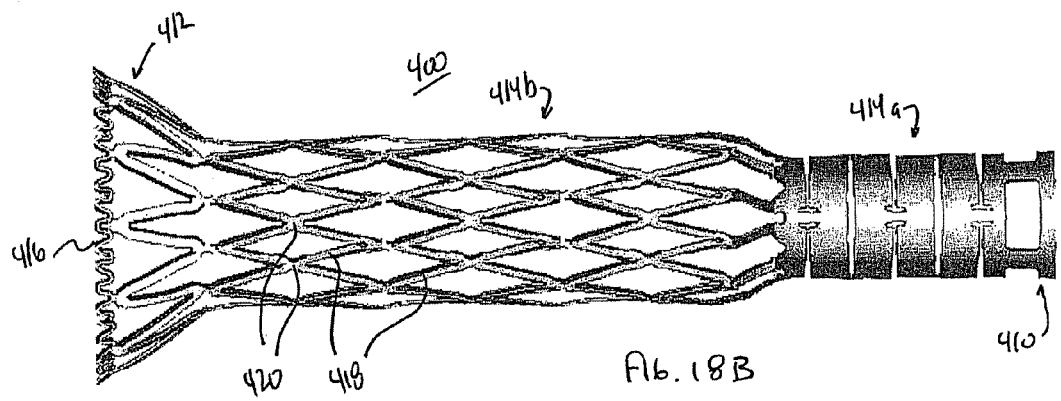
FIG. 18B is a side view of the tube of FIG. 18A in a flared state.
Figure 18C:
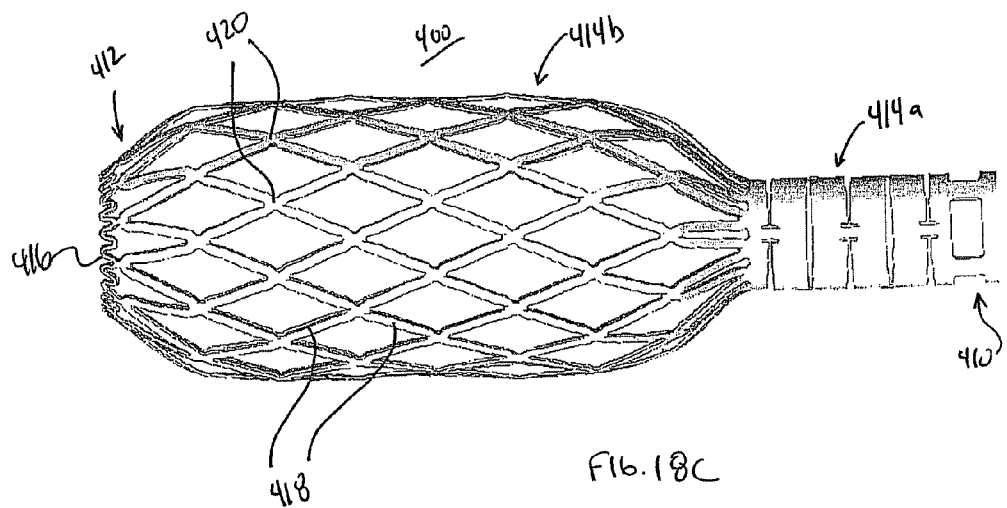
FIG. 18C is a side view of the tube of FIG. 18A in an expanded state.

FIGS. 18A-18C illustrate another laser cut tube 400 useful with the delivery capsule 28 (FIG. 3) described above. As with previous embodiments, the tube 400 is formed of a shape memory material (e.g., Nitinol) and defines a proximal zone 410, a distal zone 412, and one or more intermediate zones 414. The proximal zone 410 can be akin to the proximal zone 90 (FIG. 5A) described above, and effectuates attachment to the sheath 40 (FIG. 9). The distal zone 412 is also akin to the distal zone 92 (FIG. 5A) described above, and is configured to facilitate flaring to a distal end 416 when subjected to an internal expansion force. The first intermediate zone 414a provides for articulation or flexing as described above.

The second intermediate zone 414b is formed between the distal zone 412 and the first intermediate zone 414a, and is expandable so as to lessen the forces required for recapturing the stented heart valve prosthesis 22 (FIG. 4A). The second intermediate or expandable zone 414b can be formed as a continuation of the distal zone 412, comprised of a lattice-like or scaffolding-like arrangement. For example, a plurality of spines or struts 418 are provided, interconnected at bond points 420. In the normal or collapsed state of FIG. 18A, the distal zone 412 and the expandable zone 414b are collapsed, approximating a uniform diameter. In conjunction with the implantation methodologies described above, recapturing of a stented heart valve prosthesis can include the distal zone 412 flaring to an increased diameter at the distal end 416, effectively pivoting relative to the second intermediate zone 414a as shown in FIG. 18A. With further distal movement of the delivery capsule 28, the expandable zone 414b will expand, with the distal zone 412 collapsing about a distal end of the prosthesis as shown in FIG. 18C. Thus, the delivery capsule 28 is allowed to flare circumferentially at the distal end 416 and expand at the expandable zone 414b, thereby reducing the force required to recapture the stented heart valve prosthesis while increasing the axial strength and buckling resistance.

By way of further explanation, the tube 400 reflects an effort to reduce the force required for partially deployed transcatheter heart valve recapturing in a manner differing slightly from the tube 80 (FIG. 5A) described above. As discussed previously, it has been determined that in some instances, increasing a length of the flarable zone (e.g., the distal zone 92 (FIG. 5A)) is not viable because it may become unstable over tight bends. If distance of interface cannot be reduced, then the only way to further reduce the requisite recapture force is to reduce work required. Since work is a measure of energy expended in applying a force to move an object, the expandable zone 414b simply serves to not move the object (i.e., the stented prosthetic heart valve) as far. More particularly, with the tube 400 configuration, the prosthesis is intentionally not forced completely back to the fully collapsed state.

Figure 19A:
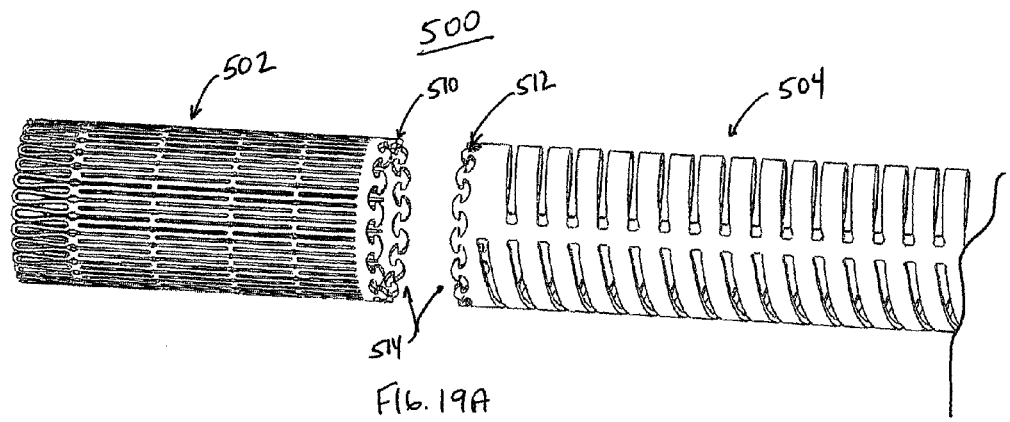
FIG. 19A is a perspective view of a portion of an alternative tube useful with the delivery capsule of FIG. 3.
Figure 19B:
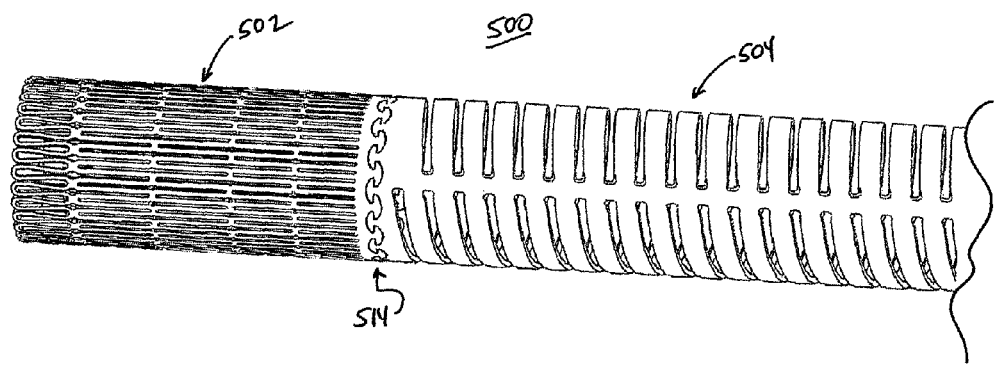
FIG. 19B is a perspective view of the tube of FIG. 19A upon final assembly.

While the tubes 80, 350, 400 have been described as being integral or homogenous bodies, in other embodiments, portions of the tube can be separately formed. With this in mind, FIGS. 19A and 19B illustrate another embodiment tube 500 useful with the delivery capsule 28 (FIG. 3). The tube 500 includes first and second tube sections 502, 504. The tube sections 502, 504 are formed (e.g., laser cut tube) separate from one another (as in FIG. 19A), and thus can have different properties (e.g., materials, wall thickness, diameters, etc.). The first tube section 502 is laser cut to have a flarable attribute, and thus is similar to any of the distal zones described above (e.g., the distal zone 92 of FIG. 5A). The second tube section 504 is laser cut to have attriculatable and columnar strength attributes, and thus is similar to any of the intermediate zones described above (e.g., the intermediate zones 94 of FIG. 5A). In addition, the first and second tube sections 502, 504 each form a complementary part 510, 512 of a locking mechanism 514 (referenced generally). For example, the locking parts 510, 512 can include a dovetail cut pattern at the end of each tube section 502, 504, with the parts 510, 512 locking to one another upon final assembly as in FIG. 19B. With the embodiment of FIGS. 19A and 19B, differently constructed tube sections 502, 504 having desired properties can be formed and easily assembled.

The heart valve replacement systems, delivery devices, and methods of present disclosure provide a marked improvement over previous designs. The delivery capsule is attached to the outer delivery. This means that there is no secondary shaft to accomplish desired recapture, and therefore does not add additional parts to the delivery device or complexity to the user. The delivery capsules are not flared in the initial, loaded state. Instead, they are "flarable" meaning that they only flare at the distal end in response to a radial force and are elastic in their flaring so that once the transcatheter heart valve is recaptured, the capsule returns to or toward its natural or unflared shape, making re-crossing of the native valve easy. In some embodiments, the delivery capsule has an expandable region which allows less force to be exerted to capture the prosthetic heart valve. With these embodiments, the expandable region need not be expanded to start with. Instead, it expands in response to a radial force and is elastic in expansion such that once the prosthetic heart valve is deployed, the delivery capsule returns to its unexpanded shape. Further, by distributing the work to collapse the stent frame cells over a greater length and minimizing the radial crimping force, the delivery capsules of the present disclosure markedly reduce occurrence of infolding of the stent frame during recapture. Also, the delivery capsules truly reduce the force on the sheath and handle to effectuate recapture, allowing for a lower profile component and thus a smaller delivery device. The flarable regions of the present disclosure have surprisingly been found to reduce the retraction force and instability by expanding, provide sufficient axial strength to not buckle while recapturing, recover to or toward a normal or unflared state following recapture, and limit a length of the flare so that the prosthesis can be functional when partially deployed. The optional flex regions of the present disclosure have surprisingly been found to provide enough columnar strength to not buckle while recapturing, provide enough flexibility to track to the deployment site without excessive force or harm to the patient, provide enough flexibility to position the stented prosthetic valve accurately and predictably, and provide sufficient radial strength and flexibility to not kink while tracking through a tortuous anatomy.

The delivery devices of the present disclosure provide for placement of a stent for replacement of an aortic valve, for example. Alternatively, the systems and devices of the present disclosure can be used for replacement of other valves and/or in other portions of the body in which a stent is to be implanted. When delivering a valved stent to replace an aortic valve, the delivery devices of the disclosure can be used with a retrograde delivery approach, for example, although it is contemplated that an antegrade delivery approach can be used, with certain modifications to the delivery device. With the systems described herein, full or partial blood flow through the valve can advantageously be maintained during the period when the valved stent is being deployed into the patient but is not yet released from its delivery device. This feature can help to prevent complications that may occur when blood flow is stopped or blocked during prosthetic valve implantation with some other known delivery devices. In addition, it is possible for the clinician to thereby evaluate the opening and closing of leaflets, examine for any paravalvular leakage and evaluate coronary flow and proper positioning of the valve within the target anatomy before final release of the valved stent.

The delivery devices shown and described herein can be modified for delivery of balloon-expandable stents, within the scope of the present disclosure. That is delivering balloon-expandable stents to an implantation location can be performed percutaneously using modified versions of the delivery devices of the disclosure. In general terms, this includes providing a transcatheter assembly which may include release sheaths and/or additional sheaths and/or collars including indentations and/or grooves, as described above. These devices can further include a delivery catheter, a balloon catheter, and/or a guide wire. A delivery catheter used in this type of device defines a lumen within which the guide wire is slidably disposed. Further, the balloon catheter includes a balloon that is fluidly connected to an inflation source. It is noted that if the stent being implanted is the self-expanding type of stent, the balloon would not be needed and a sheath or other retraining means would be used for maintaining the stent in its compressed state until deployment of the stent, as described herein. In any case, for a balloon-expandable stent, the transcatheter assembly is appropriately sized for a desired percutaneous approach to the implantation location. For example, the transcatheter assembly can be sized for delivery to the heart valve via an opening at a carotid artery, a jugular vein, a sub-clavian vein, femoral artery or vein, or the like. Essentially, any percutaneous intercostals penetration can be made to facilitate use of transcatheter assembly.

With the stent mounted to the balloon, the transcatheter assembly is delivered through a percutaneous opening (not shown) in the patient via the delivery catheter. The implantation location is located by inserting the guide wire into the patient, which guide wire extends from a distal end of the delivery catheter, with the balloon catheter otherwise retracted within the delivery catheter. The balloon catheter is then advanced distally from the delivery catheter along the guide wire, with the balloon and stent positioned relative to the implantation location. In an alternative embodiment, the stent is delivered to an implantation location via a minimally invasive surgical incision (i.e., non-percutaneously). In another alternative embodiment, the stent is delivered via open heart/chest surgery. In one embodiment of the stents of the disclosure, the stent includes a radiopaque, echogenic, or MRI visible material to facilitate visual confirmation of proper placement of the stent. Alternatively, other known surgical visual aids can be incorporated into the stent. The techniques described relative to placement of the stent within the heart can be used both to monitor and correct the placement of the stent in a longitudinal direction relative to the length of the anatomical structure in which it is positioned. Once the stent is properly positioned, the balloon catheter is operated to inflate the balloon, thus transitioning the stent to an expanded condition.

Although the present disclosure has been described with reference to preferred embodiments, workers skilled in the art will recognize that changes can be made in form and detail without departing from the spirit and scope of the present disclosure.

What is claimed is:

1. A delivery device for percutaneously deploying a stented heart valve prosthesis, the device including:

an inner shaft assembly defining a distal tip, a proximal end, and an intermediate portion providing a coupling structure configured to selectively engage a stented heart valve prosthesis;
a sheath forming a lumen sized to slidably receive at least the intermediate portion of the inner shaft assembly, the sheath terminating at a distal region; and
a tubular delivery capsule formed separately from the sheath, the capsule includes a cut tube defining:
a proximal zone attached to the distal region of the sheath,
a distal zone terminating a distal end, wherein the distal zone is configured to transition between a normal state and a flared state, a diameter of the distal end being greater in the flared state than in the normal state, the distal zone including a base opposite the distal end and a plurality of generally longitudinally extending primary splines extending from the base and each terminating at a spline distal end opposite the base, wherein the plurality of splines includes a first spline, a second spline immediately adjacent the first spline, and a third spline immediately adjacent the first spline opposite the second spline, and even further wherein the spline distal ends of the first and second splines are interconnected at a bond point, and the spline distal ends of the first and third splines are not interconnected by a bond point,
wherein the capsule includes a shape memory component constructed to naturally assume the normal state;
wherein the device is configured to slidably receive a stented heart valve prosthesis within the delivery capsule and is operable to perform a reversible partial deployment procedure in which a portion of the stented heart valve prosthesis is exposed distal the capsule and radially expands, followed by distal advancement of the capsule relative to the stented heart valve prosthesis whereby the distal zone transitions to the flared state and imparts a collapsing force onto the stented heart valve prosthesis, causing the stented heart valve prosthesis to radially collapse.

2. The device of claim 1, wherein the capsule further includes a polymer encapsulating the cut tube.

3. The device of claim 1, wherein the cut tube is formed of Nitinol.

4. The delivery device of claim 1 further comprising a handle, wherein the sheath extends distally from the handle, and further wherein the cut tube terminates at the distal region of the sheath and is distally spaced from the handle.

5. The device of claim 1, wherein the capsule further defines a first intermediate zone between the proximal and distal zones, the intermediate zone having an elevated radial flexibility as compared to at least the distal zone.

6. The device of claim 5, wherein the distal zone is formed by a first tube segment and the intermediate zone is formed by a second tube segment, and further wherein the first and second tube segments are separately formed and differ in terms of at least one attribute selected from the group consisting of material, wall thickness, and diameter.

7. The device of claim 5, wherein the capsule further defines a second intermediate zone between the distal zone and the first intermediate zone, the second intermediate zone configured to transition between a collapsed state and an expanded state, a diameter of the second intermediate zone being greater in the expanded state than in the collapsed state.

8. The device of claim 7, wherein the shape memory component of the capsule is configured to naturally assume the collapsed state.

9. The device of claim 5, wherein the cut tube is a laser cut tube that defines the plurality of primary splines to form a lattice structure along the distal zone, and forms a plurality of generally circumferentially extending, interconnected segments along the intermediate zone.

10. The device of claim 9, wherein the base is located distal the intermediate zone, and further wherein the primary splines of the distal zone extend from the base and pivot relative to the base in transitioning between the contracted and flared states.

11. The device of claim 10, wherein the laser cut tube further defines an undulating strut interconnecting circumferentially adjacent ones of the primary splines at the distal end.

12. The device of claim 9, wherein the laser cut tube further defines at least one longitudinal spine along the intermediate zone that interconnects longitudinally adjacent ones of the circumferential segments.

13. The device of claim 12, wherein the sheath includes a polymer tube maintaining at least one longitudinal sheath spine, and further wherein the at least one longitudinal spine of the tube is longitudinally aligned with at least one longitudinal delivery sheath spine.

14. The device of claim 12, wherein the intermediate zone includes two, circumferentially opposite longitudinal spines.

* * * * *